（12）United States Patent
Schreck et al.

(10) Patent No.: US 10,709,555 B2
(45) Date of Patent: Jul. 14, 2020

(54) DEVICE AND METHOD WITH REDUCED PACEMAKER RATE IN HEART VALVE REPLACEMENT

(71) Applicant: JenaValve Technology, Inc., Irvine, CA (US)

(72) Inventors: Stefan Schreck, San Clemente, CA (US); Hussain S. Rangwala, Villa Park, CA (US); Payam Saffari, Aliso Viejo, CA (US)

(73) Assignee: JenaValve Technology, Inc., Irvine, CA (US)

( * ) Notice: Subject to any disclaimer, the term of this patent is extended or adjusted under 35 U.S.C. 154(b) by 33 days.

(21) Appl. No.: 15/570,897

(22) PCT Filed: Apr. 18, 2016

(86) PCT No.: PCT/EP2016/058532
§ 371 (c)(1),
(2) Date: Oct. 31, 2017

(87) PCT Pub. No.: WO2016/177562
PCT Pub. Date: Nov. 10, 2016

(65) Prior Publication Data
US 2018/0289471 A1 Oct. 11, 2018

Related U.S. Application Data

(60) Provisional application No. 62/155,849, filed on May 1, 2015.

(51) Int. Cl.
*A61F 2/24* (2006.01)
*A61L 31/18* (2006.01)

(52) U.S. Cl.
CPC ............ *A61F 2/2418* (2013.01); *A61L 31/18* (2013.01); *A61F 2210/0014* (2013.01);
(Continued)

(58) Field of Classification Search
CPC ...... A61F 2210/0014; A61F 2220/0008; A61F 2230/0054; A61F 2230/0056;
(Continued)

(56) References Cited

U.S. PATENT DOCUMENTS 3,755,823 A 9/1973 Hancock
4,485,816 A 12/1984 Krumme
(Continued)

FOREIGN PATENT DOCUMENTS

AU 2006308187 A1 5/2007
AU 2006310681 A1 5/2007
(Continued)

OTHER PUBLICATIONS

Aortenklappenbioprothese erfolgreich in der Entwicklung, May 16, 2003 (1 page).
(Continued)

*Primary Examiner* — Paul B Prebilic
(74) *Attorney, Agent, or Firm* — Eversheds Sutherland (US) LLP

(57) ABSTRACT

The disclosure relates to heart valve prostheses with the reduced need of pacemaker implantation and improved means for positioning the replacement heart valve.

18 Claims, 17 Drawing Sheets

(52) U.S. Cl.
CPC . *A61F 2230/006* (2013.01); *A61F 2230/0013* (2013.01); *A61F 2230/0054* (2013.01); *A61F 2230/0056* (2013.01); *A61F 2250/0032* (2013.01); *A61F 2250/0097* (2013.01); *A61F 2250/0098* (2013.01)

(58) Field of Classification Search
CPC ........ A61F 2230/006; A61F 2250/0039; A61F 2250/0032; A61F 2250/0069; A61F 2250/0096–0098
See application file for complete search history.

(56) References Cited

U.S. PATENT DOCUMENTS

| | | |
|---|---|---|
| 4,502,488 A | 3/1985 | Degironimo et al. |
| 4,922,905 A | 5/1990 | Strecker |
| 4,994,077 A | 2/1991 | Dobben |
| 5,002,566 A | 3/1991 | Carpentier et al. |
| 5,026,377 A | 6/1991 | Burton et al. |
| 5,035,706 A | 7/1991 | Giantureo et al. |
| 5,053,008 A | 10/1991 | Bajaj |
| 5,061,277 A | 10/1991 | Carpentier et al. |
| 5,094,661 A | 3/1992 | Levy et al. |
| 5,104,407 A | 4/1992 | Lam et al. |
| 5,163,953 A | 11/1992 | Vince |
| 5,197,979 A | 3/1993 | Quintero et al. |
| 5,211,183 A | 5/1993 | Wilson |
| 5,234,447 A | 8/1993 | Kaster et al. |
| 5,279,612 A | 1/1994 | Eberhardt |
| 5,332,402 A | 7/1994 | Teitelbaum |
| 5,336,258 A | 8/1994 | Quintero et al. |
| 5,350,399 A | 9/1994 | Erlebacher et al. |
| 5,352,240 A | 10/1994 | Ross |
| 5,368,608 A | 11/1994 | Levy et al. |
| 5,411,552 A | 5/1995 | Andersen et al. |
| 5,429,144 A | 7/1995 | Wilk |
| 5,456,713 A | 10/1995 | Chuter |
| 5,509,930 A | 4/1996 | Love |
| 5,540,712 A | 7/1996 | Kleshinski et al. |
| 5,549,666 A | 8/1996 | Hata et al. |
| 5,595,571 A | 1/1997 | Jaffe et al. |
| 5,609,626 A | 3/1997 | Quijano et al. |
| 5,613,982 A | 3/1997 | Goldstein |
| 5,632,778 A | 5/1997 | Goldstein |
| 5,643,278 A | 7/1997 | Wijay |
| 5,655,548 A | 8/1997 | Nelson et al. |
| 5,674,298 A | 10/1997 | Levy et al. |
| 5,679,112 A | 10/1997 | Levy et al. |
| 5,683,451 A | 11/1997 | Lenker et al. |
| 5,697,972 A | 12/1997 | Kim et al. |
| 5,713,953 A | 2/1998 | Vallana et al. |
| 5,733,325 A | 3/1998 | Robinson et al. |
| 5,746,775 A | 5/1998 | Levy et al. |
| 5,755,777 A | 5/1998 | Chuter |
| 5,817,113 A | 10/1998 | Gifford, III et al. |
| 5,824,041 A | 10/1998 | Lenker et al. |
| 5,824,080 A | 10/1998 | Lamuraglia |
| 5,840,081 A | 11/1998 | Andersen et al. |
| 5,841,382 A | 11/1998 | Walden et al. |
| 5,843,181 A | 12/1998 | Jaffe et al. |
| 5,855,601 A | 1/1999 | Bessler et al. |
| 5,876,434 A | 3/1999 | Flomenblit et al. |
| 5,880,242 A | 3/1999 | Hu et al. |
| 5,885,238 A | 3/1999 | Stevens et al. |
| 5,891,160 A | 4/1999 | Williamson, IV et al. |
| 5,899,936 A | 5/1999 | Goldstein |
| 5,928,281 A | 7/1999 | Huynh et al. |
| 5,935,163 A | 8/1999 | Gabbay |
| 5,104,407 B1 | 9/1999 | Lam et al. |
| 5,957,949 A | 9/1999 | Leonhardt et al. |
| 5,987,344 A | 11/1999 | West |
| 6,001,126 A | 12/1999 | Nguyen-Thien-Nhon |
| 5,061,277 B1 | 2/2000 | Carpentier et al. |
| 6,077,297 A | 6/2000 | Robinson et al. |
| 6,093,530 A | 7/2000 | McIlroy et al. |
| 6,102,944 A | 8/2000 | Huynh et al. |
| 6,117,169 A | 9/2000 | Moe |
| 6,126,685 A | 10/2000 | Lenker et al. |
| 6,168,614 B1 | 1/2001 | Andersen et al. |
| 6,177,514 B1 | 1/2001 | Pathak et al. |
| 6,183,481 B1 | 2/2001 | Lee et al. |
| 6,200,336 B1 | 3/2001 | Pavcnik et al. |
| 6,214,055 B1 | 4/2001 | Simionescu et al. |
| 6,231,602 B1 | 5/2001 | Carpentier et al. |
| 6,241,738 B1 | 6/2001 | Dereume |
| 6,254,564 B1 | 7/2001 | Wilk et al. |
| 6,254,636 B1 | 7/2001 | Peredo |
| 6,273,876 B1 | 8/2001 | Klima et al. |
| 6,283,995 B1 | 9/2001 | Moe et al. |
| 6,287,338 B1 | 9/2001 | Sarnowski et al. |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,278 B1 | 2/2002 | Lenker et al. |
| 6,352,547 B1 | 3/2002 | Brown et al. |
| 6,379,740 B1 | 4/2002 | Rinaldi et al. |
| 6,391,538 B1 | 5/2002 | Vyavahare et al. |
| 6,425,916 B1 | 7/2002 | Garrison et al. |
| 6,454,799 B1 | 9/2002 | Schreck |
| 6,471,723 B1 | 10/2002 | Ashworth et al. |
| 6,478,819 B2 | 11/2002 | Moe |
| 6,508,833 B2 | 1/2003 | Pavcnik et al. |
| 6,509,145 B1 | 1/2003 | Torrianni |
| 6,521,179 B1 | 2/2003 | Girardot et al. |
| 6,540,782 B1 | 4/2003 | Snyders |
| 6,558,417 B2 | 5/2003 | Peredo |
| 6,558,418 B2 | 5/2003 | Carpentier et al. |
| 6,572,642 B2 | 6/2003 | Rinaldi et al. |
| 6,582,462 B1 | 6/2003 | Andersen et al. |
| 6,585,766 B1 | 7/2003 | Huynh et al. |
| 6,613,086 B1 | 9/2003 | Moe et al. |
| 6,682,559 B2 | 1/2004 | Myers et al. |
| 6,730,118 B2 | 5/2004 | Spenser et al. |
| 6,736,845 B2 | 5/2004 | Marquez et al. |
| 6,767,362 B2 | 7/2004 | Schreck |
| 6,776,791 B1 | 8/2004 | Stallings et al. |
| 6,790,230 B2 | 9/2004 | Beyersdorf et al. |
| 6,808,529 B2 | 10/2004 | Fulkerson |
| 6,821,211 B2 | 11/2004 | Otten et al. |
| 6,821,297 B2 | 11/2004 | Snyders |
| 6,824,970 B2 | 11/2004 | Vyavahare et al. |
| 6,830,584 B1 | 12/2004 | Seguin |
| 6,861,211 B2 | 3/2005 | Levy et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,945,997 B2 | 9/2005 | Huynh et al. |
| 6,974,474 B2 | 12/2005 | Pavcnik et al. |
| 7,014,655 B2 | 3/2006 | Barbarash et al. |
| 7,018,406 B2 | 3/2006 | Seguin et al. |
| 7,037,333 B2 | 5/2006 | Myers et al. |
| 7,050,276 B2 | 5/2006 | Nishiyama |
| 7,078,163 B2 | 7/2006 | Torrianni |
| 7,081,132 B2 | 7/2006 | Cook et al. |
| 7,101,396 B2 | 9/2006 | Artof et al. |
| 7,137,184 B2 | 11/2006 | Schreck et al. |
| 7,141,064 B2 | 11/2006 | Scott et al. |
| 7,163,556 B2 | 1/2007 | Xie et al. |
| 7,189,259 B2 | 3/2007 | Simionescu et al. |
| 7,198,646 B2 | 4/2007 | Figulla et al. |
| 7,201,772 B2 | 4/2007 | Schwammenthal et al. |
| 7,238,200 B2 | 7/2007 | Lee et al. |
| 7,252,682 B2 | 8/2007 | Seguin |
| 7,318,278 B2 | 1/2008 | Zhang et al. |
| 7,318,998 B2 | 1/2008 | Goldstein et al. |
| 7,322,932 B2 | 1/2008 | Xie et al. |
| 7,329,278 B2 | 2/2008 | Seguin et al. |
| 7,381,218 B2 | 6/2008 | Schreck |
| 7,393,360 B2 | 7/2008 | Spenser et al. |
| 7,399,315 B2 | 7/2008 | Iobbi |
| 7,452,371 B2 | 11/2008 | Pavcnik et al. |

(56) References Cited

U.S. PATENT DOCUMENTS

| | | | |
|---|---|---|---|
| 7,473,275 B2 | 1/2009 | Marquez | |
| 7,896,915 B2 | 3/2011 | Guyenot et al. | |
| 7,914,575 B2 | 3/2011 | Guyenot et al. | |
| 8,052,750 B2 * | 11/2011 | Tuval .................... | A61F 2/2418 623/2.17 |
| 10,321,987 B2 * | 6/2019 | Wang ..................... | A61L 27/20 |
| 10,543,084 B2 * | 1/2020 | Guyenot ............... | A61F 2/2442 |
| 2001/0011187 A1 | 8/2001 | Pavcnik et al. | |
| 2001/0021872 A1 | 9/2001 | Bailey et al. | |
| 2001/0039450 A1 | 11/2001 | Pavcnik et al. | |
| 2002/0010489 A1 | 1/2002 | Gayzel et al. | |
| 2002/0032481 A1 | 3/2002 | Gabbay | |
| 2002/0035390 A1 | 3/2002 | Schaldach et al. | |
| 2002/0045846 A1 | 4/2002 | Kaplon et al. | |
| 2002/0045929 A1 | 4/2002 | Diaz | |
| 2002/0055774 A1 * | 5/2002 | Liddicoat ............... | A61F 2/2409 623/2.4 |
| 2002/0055775 A1 | 5/2002 | Carpentier et al. | |
| 2002/0120322 A1 | 8/2002 | Thompson et al. | |
| 2002/0120323 A1 | 8/2002 | Thompson et al. | |
| 2002/0123790 A1 | 9/2002 | White et al. | |
| 2002/0133226 A1 | 9/2002 | Marquez et al. | |
| 2002/0143387 A1 | 10/2002 | Soetikno et al. | |
| 2002/0151970 A1 | 10/2002 | Garrison et al. | |
| 2002/0161426 A1 | 10/2002 | Iancea | |
| 2002/0177840 A1 | 11/2002 | Farnholtz | |
| 2002/0198594 A1 | 12/2002 | Schreck | |
| 2003/0027332 A1 | 2/2003 | Lafrance et al. | |
| 2003/0036791 A1 | 2/2003 | Philipp et al. | |
| 2003/0036795 A1 | 2/2003 | Andersen et al. | |
| 2003/0040792 A1 | 2/2003 | Gabbay | |
| 2003/0050694 A1 | 3/2003 | Yang et al. | |
| 2003/0055495 A1 | 3/2003 | Pease et al. | |
| 2003/0065386 A1 | 4/2003 | Weadock | |
| 2003/0114913 A1 | 6/2003 | Spenser et al. | |
| 2003/0125795 A1 | 7/2003 | Pavcnik et al. | |
| 2003/0139796 A1 | 7/2003 | Sequin et al. | |
| 2003/0139803 A1 | 7/2003 | Sequin et al. | |
| 2003/0149476 A1 | 8/2003 | Damm et al. | |
| 2003/0153974 A1 | 8/2003 | Spenser et al. | |
| 2003/0195620 A1 | 10/2003 | Huynh et al. | |
| 2003/0236570 A1 | 12/2003 | Cook et al. | |
| 2004/0006380 A1 | 1/2004 | Buck et al. | |
| 2004/0039436 A1 | 2/2004 | Spenser et al. | |
| 2004/0049262 A1 | 3/2004 | Obermiller et al. | |
| 2004/0073289 A1 | 4/2004 | Hartley et al. | |
| 2004/0078950 A1 | 4/2004 | Schreck et al. | |
| 2004/0093060 A1 | 5/2004 | Seguin et al. | |
| 2004/0093063 A1 | 5/2004 | Wright et al. | |
| 2004/0117004 A1 | 6/2004 | Osborne et al. | |
| 2004/0117009 A1 | 6/2004 | Cali et al. | |
| 2004/0148018 A1 | 7/2004 | Carpentier et al. | |
| 2004/0153145 A1 | 8/2004 | Simionescu et al. | |
| 2004/0186558 A1 | 9/2004 | Pavcnik et al. | |
| 2004/0186563 A1 | 9/2004 | Lobbi | |
| 2004/0186565 A1 | 9/2004 | Schreck | |
| 2004/0193244 A1 | 9/2004 | Hartley et al. | |
| 2004/0206363 A1 | 10/2004 | McCarthy et al. | |
| 2004/0210301 A1 | 10/2004 | Obermiller | |
| 2004/0210304 A1 | 10/2004 | Seguin et al. | |
| 2004/0210306 A1 | 10/2004 | Quijano et al. | |
| 2004/0243143 A1 | 12/2004 | Corcoran et al. | |
| 2004/0249343 A1 | 12/2004 | Cioanta | |
| 2004/0260389 A1 | 12/2004 | Case et al. | |
| 2005/0009000 A1 | 1/2005 | Wilhelm et al. | |
| 2005/0033220 A1 | 2/2005 | Wilk et al. | |
| 2005/0033398 A1 | 2/2005 | Seguin | |
| 2005/0043790 A1 | 2/2005 | Seguin | |
| 2005/0049692 A1 | 3/2005 | Numamoto et al. | |
| 2005/0060018 A1 | 3/2005 | Dittman | |
| 2005/0075725 A1 | 4/2005 | Rowe | |
| 2005/0075776 A1 | 4/2005 | Cho | |
| 2005/0096726 A1 | 5/2005 | Sequin et al. | |
| 2005/0096736 A1 | 5/2005 | Osse et al. | |
| 2005/0098547 A1 | 5/2005 | Cali et al. | |
| 2005/0113902 A1 | 5/2005 | Geiser et al. | |
| 2005/0113910 A1 | 5/2005 | Paniagua et al. | |
| 2005/0119728 A1 | 6/2005 | Sarac | |
| 2005/0119736 A1 | 6/2005 | Zilla et al. | |
| 2005/0125075 A1 | 6/2005 | Meade et al. | |
| 2005/0137499 A1 | 6/2005 | Sheets et al. | |
| 2005/0137609 A1 | 6/2005 | Guiraudon | |
| 2005/0137682 A1 | 6/2005 | Justino | |
| 2005/0137687 A1 | 6/2005 | Salahieh et al. | |
| 2005/0137688 A1 | 6/2005 | Salahieh et al. | |
| 2005/0137689 A1 * | 6/2005 | Salahieh ............... | A61F 2/2418 623/2.11 |
| 2005/0137690 A1 | 6/2005 | Salahieh et al. | |
| 2005/0137697 A1 | 6/2005 | Salahieh et al. | |
| 2005/0137698 A1 | 6/2005 | Salahieh et al. | |
| 2005/0137702 A1 | 6/2005 | Haug et al. | |
| 2005/0143804 A1 | 6/2005 | Haverkost | |
| 2005/0143807 A1 | 6/2005 | Pavcnik et al. | |
| 2005/0149166 A1 | 7/2005 | Schaeffer et al. | |
| 2005/0150775 A1 | 7/2005 | Zhang et al. | |
| 2005/0171597 A1 | 8/2005 | Boatman et al. | |
| 2005/0171598 A1 | 8/2005 | Schaeffer | |
| 2005/0192665 A1 | 9/2005 | Spenser et al. | |
| 2005/0197695 A1 | 9/2005 | Stacchino et al. | |
| 2005/0222668 A1 | 10/2005 | Schaeffer et al. | |
| 2005/0234546 A1 | 10/2005 | Nugent et al. | |
| 2005/0267560 A1 | 12/2005 | Bates | |
| 2006/0009842 A1 | 1/2006 | Huynh et al. | |
| 2006/0025857 A1 | 2/2006 | Bergheim et al. | |
| 2006/0047343 A1 | 3/2006 | Oviatt et al. | |
| 2006/0058864 A1 | 3/2006 | Schaeffer et al. | |
| 2006/0074484 A1 | 4/2006 | Huber | |
| 2006/0111770 A1 | 5/2006 | Pavcnik et al. | |
| 2006/0136034 A1 | 6/2006 | Modesitt et al. | |
| 2006/0142846 A1 | 6/2006 | Pavcnik et al. | |
| 2006/0149360 A1 | 7/2006 | Schwammenthal et al. | |
| 2006/0155366 A1 | 7/2006 | LaDuca et al. | |
| 2006/0167543 A1 | 7/2006 | Bailey et al. | |
| 2006/0193885 A1 | 8/2006 | Neethling et al. | |
| 2006/0210597 A1 | 9/2006 | Hiles | |
| 2006/0224183 A1 | 10/2006 | Freudenthal | |
| 2006/0229561 A1 | 10/2006 | Huszar | |
| 2006/0229718 A1 | 10/2006 | Marquez | |
| 2006/0229719 A1 | 10/2006 | Marquez et al. | |
| 2006/0246584 A1 | 11/2006 | Covelli | |
| 2006/0259134 A1 | 11/2006 | Schwammenthal et al. | |
| 2006/0259136 A1 | 11/2006 | Nguyen et al. | |
| 2006/0259137 A1 | 11/2006 | Artof et al. | |
| 2006/0265056 A1 | 11/2006 | Nguyen et al. | |
| 2006/0287717 A1 | 12/2006 | Rowe et al. | |
| 2006/0287719 A1 | 12/2006 | Rowe et al. | |
| 2006/0290027 A1 | 12/2006 | O'Connor et al. | |
| 2006/0293745 A1 | 12/2006 | Carpentier et al. | |
| 2007/0005129 A1 | 1/2007 | Damm et al. | |
| 2007/0005131 A1 | 1/2007 | Taylor | |
| 2007/0005132 A1 | 1/2007 | Simionescu et al. | |
| 2007/0020248 A1 | 1/2007 | Everaerts et al. | |
| 2007/0021826 A1 | 1/2007 | Case et al. | |
| 2007/0027535 A1 | 2/2007 | Purdy, Jr. et al. | |
| 2007/0038291 A1 | 2/2007 | Case et al. | |
| 2007/0038295 A1 | 2/2007 | Case et al. | |
| 2007/0043435 A1 | 2/2007 | Seguin et al. | |
| 2007/0050014 A1 | 3/2007 | Johnson | |
| 2007/0056346 A1 | 3/2007 | Spenser et al. | |
| 2007/0088431 A1 | 4/2007 | Bourang et al. | |
| 2007/0093887 A1 | 4/2007 | Case et al. | |
| 2007/0100435 A1 | 5/2007 | Case et al. | |
| 2007/0100440 A1 | 5/2007 | Figulla et al. | |
| 2007/0112422 A1 | 5/2007 | Dehdashtian | |
| 2007/0123700 A1 | 5/2007 | Ueda et al. | |
| 2007/0123979 A1 | 5/2007 | Perier et al. | |
| 2007/0142906 A1 | 6/2007 | Figulla et al. | |
| 2007/0162103 A1 | 7/2007 | Case et al. | |
| 2007/0173932 A1 | 7/2007 | Cali et al. | |
| 2007/0179592 A1 | 8/2007 | Schaeffer | |
| 2007/0185565 A1 | 8/2007 | Schwammenthal et al. | |
| 2007/0203576 A1 | 8/2007 | Lee et al. | |
| 2007/0213813 A1 | 9/2007 | Von Segesser et al. | |
| 2007/0239271 A1 | 10/2007 | Nguyen | |

(56) References Cited

U.S. PATENT DOCUMENTS

| | | |
|---|---|---|
| 2007/0244551 A1 | 10/2007 | Stobie |
| 2007/0260327 A1 | 11/2007 | Case et al. |
| 2007/0288087 A1 | 12/2007 | Fearnot et al. |
| 2008/0004688 A1 | 1/2008 | Spenser et al. |
| 2008/0021546 A1 | 1/2008 | Patz et al. |
| 2008/0022504 A1 | 1/2008 | Melsheimer |
| 2008/0033534 A1 | 2/2008 | Cook et al. |
| 2008/0039934 A1* | 2/2008 | Styrc ............... A61F 2/2409 623/2.17 |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077236 A1 | 3/2008 | Letac et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0127707 A1 | 6/2008 | Kokish et al. |
| 2008/0133003 A1 | 6/2008 | Seguin et al. |
| 2008/0140189 A1 | 6/2008 | Nguyen et al. |
| 2008/0147182 A1 | 6/2008 | Righini et al. |
| 2008/0154355 A1 | 6/2008 | Benichou et al. |
| 2008/0200977 A1 | 8/2008 | Paul et al. |
| 2008/0215143 A1 | 9/2008 | Seguin |
| 2008/0221703 A1 | 9/2008 | Que et al. |
| 2008/0255660 A1 | 10/2008 | Guyenot et al. |
| 2008/0255661 A1 | 10/2008 | Straubinger et al. |
| 2008/0262602 A1 | 10/2008 | Wilk et al. |
| 2008/0269878 A1 | 10/2008 | Iobbi |
| 2008/0275549 A1 | 11/2008 | Rowe |
| 2009/0093876 A1 | 4/2009 | Nitzan et al. |
| 2009/0192591 A1* | 7/2009 | Ryan ............... A61F 2/2412 623/1.26 |
| 2009/0216312 A1 | 8/2009 | Straubinger et al. |
| 2009/0222076 A1 | 9/2009 | Figulla et al. |
| 2010/0082094 A1* | 4/2010 | Quadri ............ A61F 2/2412 623/1.26 |
| 2010/0100167 A1 | 4/2010 | Bortlein et al. |
| 2010/0160725 A1 | 6/2010 | Kiser et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0262231 A1 | 10/2010 | Tuval et al. |
| 2011/0093007 A1 | 4/2011 | Abbott et al. |
| 2011/0208290 A1 | 8/2011 | Straubinger et al. |
| 2011/0208297 A1 | 8/2011 | Tuval et al. |
| 2011/0319989 A1 | 12/2011 | Lane et al. |
| 2012/0078360 A1* | 3/2012 | Rafiee ............... A61F 2/2418 623/2.37 |
| 2014/0236287 A1* | 8/2014 | Clague ............. A61F 2/2418 623/2.11 |
| 2016/0051362 A1* | 2/2016 | Cooper ............. A61F 2/2418 623/2.18 |
| 2020/0054449 A1* | 2/2020 | Min .................. A61F 2/848 |

FOREIGN PATENT DOCUMENTS

| | | |
|---|---|---|
| CA | 2436258 A1 | 1/2005 |
| CA | 2595233 A1 | 7/2006 |
| CA | 2627555 | 5/2007 |
| CN | 1745727 A | 3/2006 |
| CN | 2762776 Y | 3/2006 |
| CN | 1897892 A | 1/2007 |
| CN | 2933337 Y | 8/2007 |
| CN | 101431963 A | 5/2009 |
| CN | 101605509 A | 12/2009 |
| CN | 101623217 A | 1/2010 |
| CN | 101700199 A | 5/2010 |
| CN | 101720211 A | 6/2010 |
| CN | 102271626 A | 12/2011 |
| DE | 4316971 A1 | 11/1994 |
| DE | 19532846 A1 | 3/1997 |
| DE | 19546692 A1 | 6/1997 |
| DE | 19633901 A1 | 2/1998 |
| DE | 20003874 U1 | 6/2000 |
| DE | 19857887 A1 | 7/2000 |
| DE | 10010073 A1 | 9/2001 |
| DE | 10010074 A1 | 10/2001 |
| DE | 10034105 C1 | 4/2002 |
| DE | 101 21 210 A1 | 11/2002 |
| DE | 19546692 C2 | 11/2002 |
| DE | 10301026 A1 | 2/2004 |
| DE | 10302447 A1 | 7/2004 |
| DE | 10335948 B3 | 2/2005 |
| DE | 10010074 B4 | 4/2005 |
| DE | 19857887 B4 | 5/2005 |
| DE | 10010073 B4 | 12/2005 |
| DE | 10 2005 051 849 | 5/2007 |
| DE | 10 2005 052628 A1 | 5/2007 |
| DE | 20 2007 005 491 U1 | 7/2007 |
| DE | 20221871 U1 | 10/2008 |
| EP | 0084395 A1 | 7/1983 |
| EP | 0402036 B1 | 12/1990 |
| EP | 0402176 B1 | 12/1990 |
| EP | 0411118 A1 | 2/1991 |
| EP | 0458877 B1 | 4/1991 |
| EP | 0515324 A1 | 11/1992 |
| EP | 0547135 B1 | 6/1993 |
| EP | 0657147 A2 | 6/1995 |
| EP | 0 592 410 B1 | 10/1995 |
| EP | 0 592 410 B1 | 11/1995 |
| EP | 0729364 B1 | 9/1996 |
| EP | 0756498 B1 | 5/1997 |
| EP | 0778775 B1 | 6/1997 |
| EP | 0826346 A1 | 3/1998 |
| EP | 0896813 A2 | 2/1999 |
| EP | 0903122 A2 | 3/1999 |
| EP | 0928615 A1 | 7/1999 |
| EP | 0938877 A2 | 9/1999 |
| EP | 0986348 B1 | 3/2000 |
| EP | 1 251 805 B1 | 10/2000 |
| EP | 1041942 B1 | 10/2000 |
| EP | 1041943 B1 | 10/2000 |
| EP | 1117446 B1 | 7/2001 |
| EP | 1 233 731 B1 | 5/2002 |
| EP | 1206179 B1 | 5/2002 |
| EP | 1251804 B1 | 10/2002 |
| EP | 0 971 649 B1 | 12/2002 |
| EP | 1281357 A2 | 2/2003 |
| EP | 1281375 A2 | 2/2003 |
| EP | 1 017 868 B1 | 9/2003 |
| EP | 1354569 A1 | 10/2003 |
| EP | 1452153 A1 | 9/2004 |
| EP | 0987998 B1 | 10/2004 |
| EP | 1 087 727 B1 | 11/2004 |
| EP | 1499366 B1 | 1/2005 |
| EP | 1518518 A2 | 3/2005 |
| EP | 1 253 875 B1 | 4/2005 |
| EP | 1 251 803 B1 | 6/2005 |
| EP | 1469797 B1 | 11/2005 |
| EP | 1 690 515 A1 | 8/2006 |
| EP | 1 255 510 B1 | 3/2007 |
| EP | 1112042 B1 | 11/2007 |
| EP | 1878407 A1 | 1/2008 |
| EP | 1886649 A2 | 2/2008 |
| EP | 1 900 343 A2 | 3/2008 |
| EP | 1259195 B1 | 10/2008 |
| EP | 1980220 A1 | 10/2008 |
| EP | 1994913 A2 | 11/2008 |
| EP | 2 000 115 A2 | 12/2008 |
| EP | 2474287 A1 | 7/2012 |
| EP | 3028668 A1 | 6/2016 |
| FR | 2788217 A1 | 7/2000 |
| FR | 2815844 A1 | 5/2002 |
| FR | 2828263 A1 | 2/2003 |
| GB | 2433700 A | 7/2007 |
| GB | 2440809 A | 2/2008 |
| JP | 52-86296 | 7/1977 |
| JP | 62-227352 | 10/1987 |

(56) References Cited

FOREIGN PATENT DOCUMENTS

| | | |
|---|---|---|
| JP | 1049571 A | 2/1989 |
| JP | 7-504091 | 5/1995 |
| JP | 2001-526574 A | 12/2001 |
| JP | 2004-504111 A | 2/2002 |
| JP | 2002-525168 A | 8/2002 |
| JP | 2002-525169 A | 8/2002 |
| JP | 2002-536115 A | 10/2002 |
| JP | 2003-515386 A | 5/2003 |
| JP | 2003-523262 | 8/2003 |
| JP | 2003-524504 | 8/2003 |
| JP | 2004-283461 A | 10/2004 |
| JP | 2005-118585 | 5/2005 |
| JP | 2007-521125 A | 8/2007 |
| JP | 2007-296375 | 11/2007 |
| JP | 2008-539985 A | 11/2008 |
| JP | 2009-131397 A | 6/2009 |
| JP | 2009-534157 A | 9/2009 |
| JP | 2010-526609 A | 8/2010 |
| WO | WO 92/12690 | 8/1982 |
| WO | WO-90/09102 | 8/1990 |
| WO | WO 91/17720 A1 | 11/1991 |
| WO | WO 95/11055 A1 | 4/1995 |
| WO | WO-95/24873 | 9/1995 |
| WO | WO-95/28183 | 10/1995 |
| WO | WO 95/29713 A1 | 11/1995 |
| WO | WO-96/13227 | 5/1996 |
| WO | WO 97/27893 A1 | 8/1997 |
| WO | WO 97/27898 A1 | 8/1997 |
| WO | WO-97/32615 | 9/1997 |
| WO | WO 98/08456 A1 | 3/1998 |
| WO | WO 98/11846 A1 | 3/1998 |
| WO | WO 98/19633 A1 | 5/1998 |
| WO | WO 98/43556 | 10/1998 |
| WO | WO-98/46165 | 10/1998 |
| WO | WO 98/53761 A1 | 12/1998 |
| WO | WO 99/36001 A1 | 7/1999 |
| WO | WO-99/37337 | 7/1999 |
| WO | WO 99/42058 A1 | 8/1999 |
| WO | WO 99/53987 A1 | 10/1999 |
| WO | WO-99/66863 | 12/1999 |
| WO | WO 00/02503 A1 | 1/2000 |
| WO | WO 00/15148 | 3/2000 |
| WO | WO 00/18330 | 4/2000 |
| WO | WO 00/18333 A1 | 4/2000 |
| WO | WO-00/18445 | 4/2000 |
| WO | WO 00/21464 A1 | 4/2000 |
| WO | WO 2000/25702 A1 | 5/2000 |
| WO | WO 00/47139 A1 | 8/2000 |
| WO | WO-00/53125 | 9/2000 |
| WO | WO-00/62714 | 10/2000 |
| WO | WO 00/69367 A1 | 11/2000 |
| WO | WO 00/78226 A1 | 12/2000 |
| WO | WO-01/10209 A1 | 2/2001 |
| WO | WO 2001/35870 A1 | 5/2001 |
| WO | WO-01/41679 A1 | 6/2001 |
| WO | WO 2001/039700 A1 | 6/2001 |
| WO | WO 01/49213 A2 | 7/2001 |
| WO | WO-01/51104 A1 | 7/2001 |
| WO | WO 01/54625 A1 | 8/2001 |
| WO | WO-01/58503 A1 | 8/2001 |
| WO | WO 01/62189 A1 | 8/2001 |
| WO | WO 01/64137 A1 | 9/2001 |
| WO | WO 02/22054 A1 | 3/2002 |
| WO | WO 2002/36048 A1 | 5/2002 |
| WO | WO-02/058745 A1 | 8/2002 |
| WO | WO-02/100301 A1 | 12/2002 |
| WO | WO-02/102286 A1 | 12/2002 |
| WO | WO 03/003949 A2 | 1/2003 |
| WO | WO-03/007795 A2 | 1/2003 |
| WO | WO 2003/003949 A2 | 1/2003 |
| WO | WO-03/009785 A1 | 2/2003 |
| WO | WO 03/013239 | 2/2003 |
| WO | WO 2003/011195 A2 | 2/2003 |
| WO | WO 03/028592 A1 | 4/2003 |
| WO | WO 03/047468 A1 | 6/2003 |
| WO | WO 03/051231 A2 | 6/2003 |
| WO | WO-03/079928 A2 | 10/2003 |
| WO | WO 03/079933 A1 | 10/2003 |
| WO | WO 03/092554 A1 | 11/2003 |
| WO | WO 2003/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO 2004/019825 A1 | 3/2004 |
| WO | WO-2004/026117 A2 | 4/2004 |
| WO | WO 2004/026173 A2 | 4/2004 |
| WO | WO 2004/028399 A2 | 4/2004 |
| WO | WO 2004/030515 A2 | 4/2004 |
| WO | WO 2004/043301 A1 | 5/2004 |
| WO | WO 2004/064671 A2 | 8/2004 |
| WO | WO 2004/082527 A2 | 9/2004 |
| WO | WO 2004/082528 A2 | 9/2004 |
| WO | WO 2004/096100 A1 | 11/2004 |
| WO | WO 2005/011534 A1 | 2/2005 |
| WO | WO 2005/021063 A2 | 3/2005 |
| WO | WO 2005/034812 A1 | 4/2005 |
| WO | WO 2005/062980 A2 | 7/2005 |
| WO | WO 2005/063980 A1 | 7/2005 |
| WO | WO 2005/070343 A1 | 8/2005 |
| WO | WO-2005/072654 A1 | 8/2005 |
| WO | WO 2005/102015 A2 | 11/2005 |
| WO | WO 2006/066327 | 6/2006 |
| WO | WO-2006/066327 A1 | 6/2006 |
| WO | WO 2006/070372 A2 | 7/2006 |
| WO | WO 2006/076890 | 7/2006 |
| WO | WO 2006/089517 A1 | 8/2006 |
| WO | WO-2006/102063 A2 | 9/2006 |
| WO | WO 2006/108090 A2 | 10/2006 |
| WO | WO 2006/124649 A2 | 11/2006 |
| WO | WO-2006/124649 A2 | 11/2006 |
| WO | WO 2006/127756 A2 | 11/2006 |
| WO | WO 2006/127765 A1 | 11/2006 |
| WO | WO 2006/129441 A1 | 12/2006 |
| WO | WO-2006/132948 A1 | 12/2006 |
| WO | WO 2006/133959 A1 | 12/2006 |
| WO | WO 2007/047488 A2 | 4/2007 |
| WO | WO 2007/047945 A2 | 4/2007 |
| WO | WO 2007/048529 A1 | 5/2007 |
| WO | WO-2007/048529 A1 | 5/2007 |
| WO | WO 2007/051620 A1 | 5/2007 |
| WO | WO-2007/071436 A2 | 6/2007 |
| WO | WO 2007/098232 A2 | 8/2007 |
| WO | WO 2007/120543 A1 | 10/2007 |
| WO | WO 2007/123956 | 11/2007 |
| WO | WO-2008/028569 A1 | 3/2008 |
| WO | WO 2008/035337 A2 | 3/2008 |
| WO | WO 2008/045949 | 4/2008 |
| WO | WO 2008/051554 A2 | 5/2008 |
| WO | WO 2008/070797 A2 | 6/2008 |
| WO | WO 2008/079962 A1 | 7/2008 |
| WO | WO 2008/098191 A2 | 8/2008 |
| WO | WO 2008/101083 A2 | 8/2008 |
| WO | WO 2008/125153 A1 | 10/2008 |
| WO | WO 2008/138584 A1 | 11/2008 |
| WO | WO 2008/150529 A1 | 12/2008 |
| WO | WO 2009/053497 A1 | 4/2009 |
| WO | WO 2009/094188 A2 | 7/2009 |
| WO | WO 2009/094501 A1 | 7/2009 |
| WO | WO 2009/106545 A1 | 9/2009 |
| WO | WO 2009/149462 A2 | 12/2009 |
| WO | WO 2011/008812 A2 | 1/2011 |
| WO | WO 2011/060386 A2 | 5/2011 |
| WO | WO 2011/104269 A1 | 9/2011 |
| WO | WO 2011/120050 A1 | 9/2011 |
| WO | WO 2011/144351 A2 | 11/2011 |
| WO | WO 2011/147849 A1 | 12/2011 |
| WO | WO 2012/023980 A1 | 2/2012 |
| WO | WO 2012/036742 A2 | 3/2012 |
| WO | WO 2012/038550 A1 | 3/2012 |
| WO | WO 2012/039748 A2 | 3/2012 |

(56) References Cited

FOREIGN PATENT DOCUMENTS

| WO | WO 2012/082952 A2 | 6/2012 |
| WO | WO 2012/106491 A1 | 8/2012 |
| WO | WO 2012/142189 A1 | 10/2012 |
| WO | WO 2015/028209 A1 | 3/2015 |
| WO | WO 2016/093877 A1 | 6/2016 |

OTHER PUBLICATIONS

English translation of Aortenklappenbioprothese erfolgreich in der Entwicklung (2 pages), (May 2003).

Ferrari, "Entwicklung eines Verfahrens zum transvaskulären Aortenklappenersatz," Habilitationsschrift, Medizinische Fakultät der Friedrich-Schiller-Universität Jena, pp. 49-52, dated Sep. 2003.

Ferrari, "Entwicklung eines Verfahrens zum transvaskulären Aortenklappenersatz," Habilitationsschrift, Medizinische Fakultät der Friedrich-Schiller-Universität Jena, pp. 1-159, dated Sep. 2003.

International Search Report for PCT/EP2016/058532, dated Jul. 11, 2016 (4 pages).

Liang, Ma, et al., "Double-crowned valved stents for off-pump mitral valve replacement," *Eur. J. Cardio-Thoracic Surgery*, vol. 28, pp. 194-198 (2005) (5 pages); Aug. 2005.

Huber, Christoph H., et al. "Direct Access Valve Replacement (DAVR)—are we entering a new era in cardiac surgery?" *Eur. J. Cardio-Thoracic Surgery*, vol. 29, pp. 380-385 (2006) (6 pages); received Mar. 2006.

Klein, Allan L. et al., "Age-related Prevalence of Valvular Regurgitation in Normal Subjects: A Comprehensive Color Flow Examination of 118 Volunteers," *J. Am. Soc. Echocardiography*, vol. 3, No. 1, pp. 54-63 (1990) (10 pages), Jan.-Feb. 1990.

Gummert, J.F. et al., "Cardiac Surgery in Germany During 2007: A Report on Behalf of the German Society for Thoracic and Cardiovascular Surgery," *Thorac. Cardiov. Surg.*, vol. 56, pp. 328-336 (2008) (9 pages), Sep. 2008.

Gummert, J.F. et al., "Cardiac Surgery in Germany During 2006: A Report on Behalf of the German Society for Thoracic and Cardiovascular Surgery," *Thorac. Cardiov. Surg.*, vol. 55, pp. 343-350 (2007) (8 pages), Sep. 2007.

Ferrari, M.W. et al., "Transarterial Aortic Valve Replacement with a Self expanding Stent in Pigs," *Heart*, vol. 90, No. 11, pp. 1326-1331 (2004), Nov. 2004.

\* cited by examiner

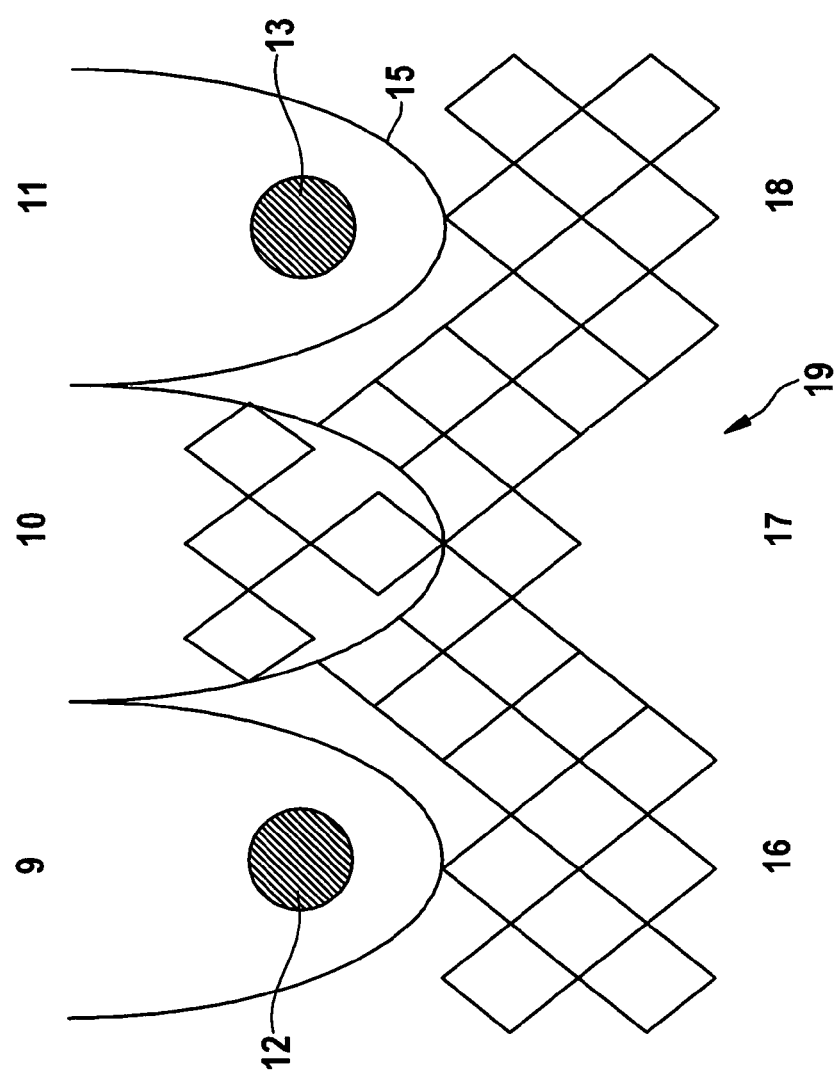

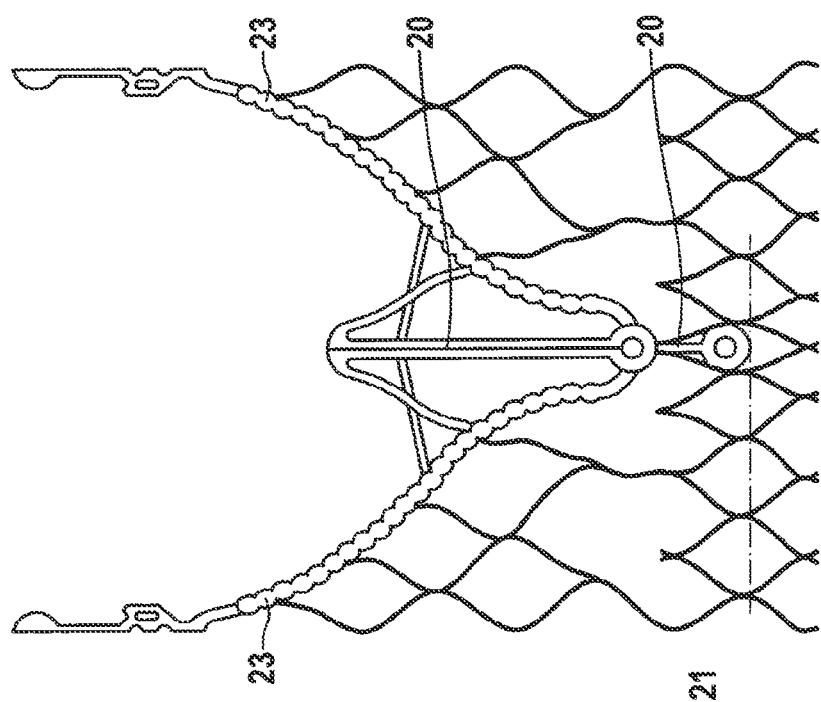
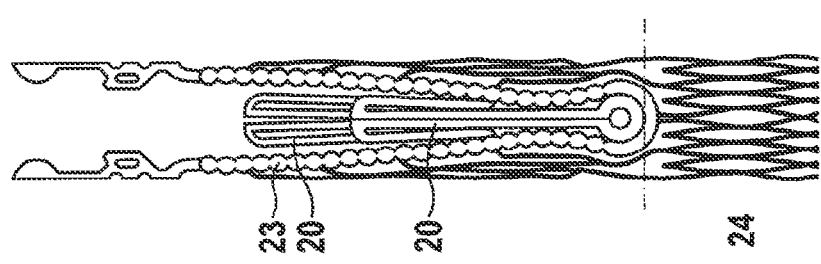
FIG. 5B
FIG. 5A

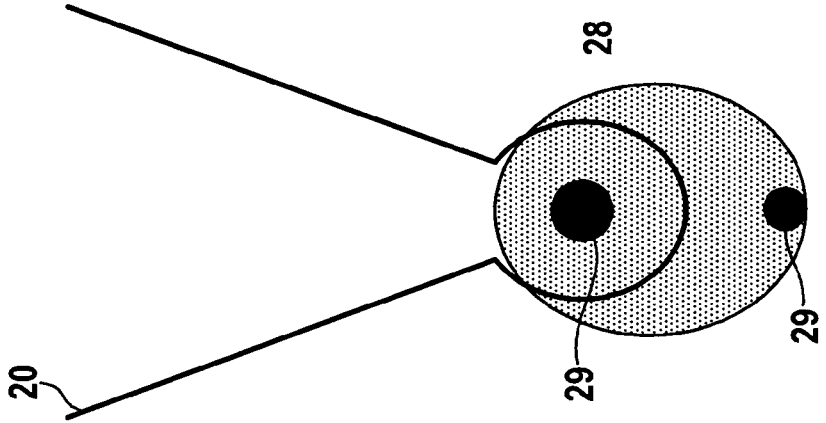
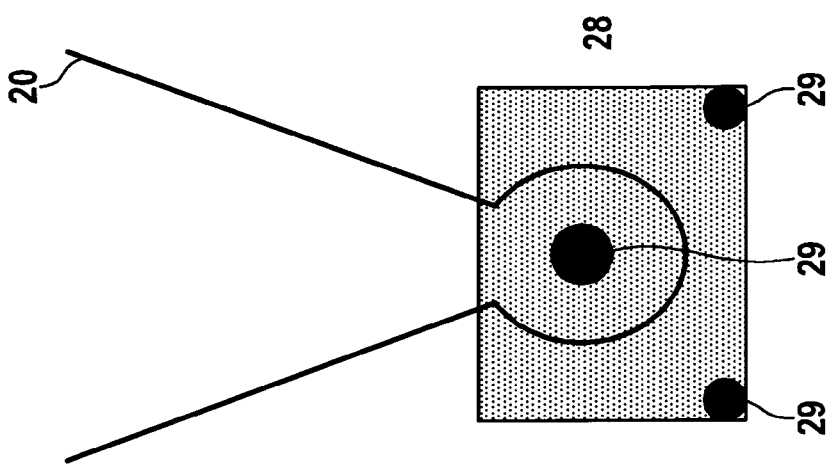
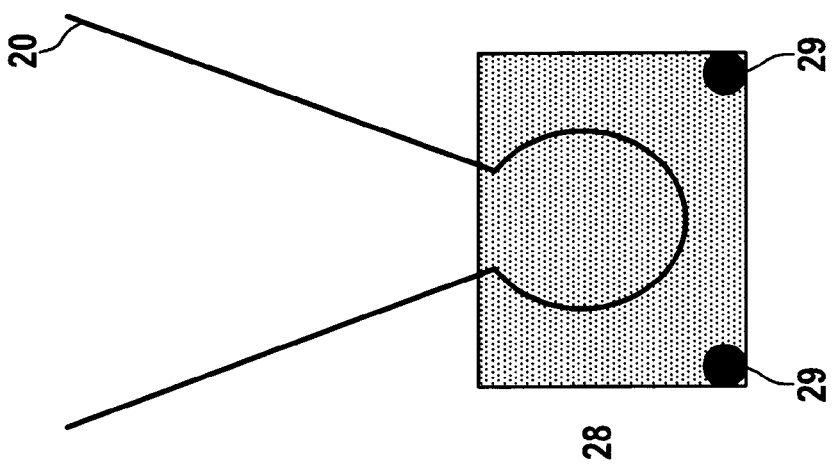

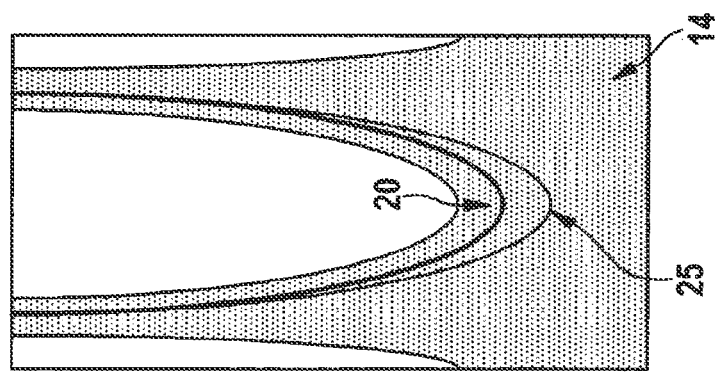
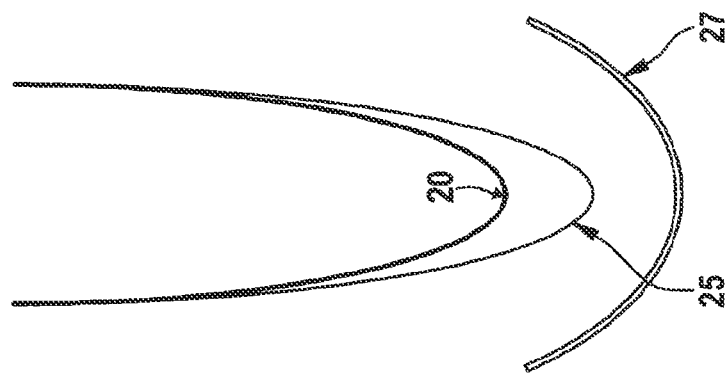
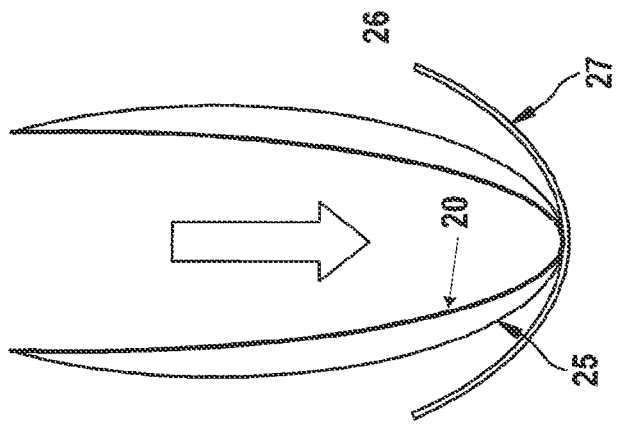

DEVICE AND METHOD WITH REDUCED PACEMAKER RATE IN HEART VALVE REPLACEMENT

This application is a national stage filing under 35 U.S.C. § 371 of International Application No. PCT/EP2016/058532 filed on Apr. 18, 2016, which published in the English language and claims the benefit of priority to U.S. Provisional Application No. 62/155,849 filed on May 1, 2015.

The present disclosure relates to heart valve prostheses with reduced pace maker rate and means and methods for visualization of the correct implantation of a medical device at the target site in a patient.

BACKGROUND

A number of applications have been established making use of medical devices, which can be delivered by way of minimally invasive methods in a patient. An example of such a medical device is a heart valve prosthesis.

Various replacement heart valves for aortic, mitral and tricuspid heart valves are currently available. In particular in the context of aortic heart valves replacement valves a side effect is the necessity of pace maker implantation in many implantations and devices. The requirement of a pacemaker can be as high as 30% in state of the art device implantation. This does not only have the drawback of another surgery and medical device with all its negative implications for the patient but also imposes increased cost in the context of such a heart valve replacement therapy. Accordingly there is a need to avoid or at least reduce the rate of pacemakers in such treatments.

Another problem often occurs when trying to achieving a correct implantation and positioning of the prosthesis at the target site in order to fully and reliably exhibit the prosthesis' function.

A particular example is a catheter-based aortic valve prosthesis consisting of a self-expanding stent and a valve known for treating aortic insufficiency. Such heart valve prostheses are positioned at the aortic annulus to replace the endogenous aortic valve. The aim is to correctly position the heart valve prosthesis with regard to the aortic annulus and the endogenous cusps.

WO2004/019825 describes an aortic prosthesis wherein the prosthesis exhibits feelers which are meant to be deployed first and placed into the aortic cusps. Once the feelers have been placed within the cusps the stent is deployed to complete the implantation. The entire implant procedure is guided by fluoroscopic imaging. The stent and feelers are visible under fluoroscopy. The aorta, aortic valve, and left ventricle are visualized indirectly by injecting contrast medium through an angiographic catheter into the left ventricle and ascending aorta. During valve deployment the angiographic catheters are retracted to avoid interference between the stent and the angiographic catheter. Thus, the operator mainly relies on tactile feedback for feeler placement.

In case of a transfemoral valve replacement, the tactile feedback may be inconsistent due to the tortuosity of the access vessels and the curvature of the aortic arch. As a result, the prosthesis may not be placed sufficiently correct at its target site. In case a prosthesis is applied that uses feelers, cusp positioners, hooks, rims or similar means to provide for precise positioning and/or targeting the endogenous leaflet cusps, these means may not be correctly positioned and/or they may be placed away from the base of the cusps or may damage the cusps.

There exists thus the need for better guiding the placement of the valve prosthesis and to avoid damage of the endogenous heart tissue and in particular cusp damage or perforation.

Another issue is leakage of blood between the replacement heart valve and the endogenous tissue e.g. at the annular ring of the aortic heart valve. Known prostheses try to improve leak tightness by applying or forming a ring or band along the annular ring and cover the prosthesis by a symmetric band made of biological or synthetic tissue. Some disclosures try to improve the leak tightness with the combination of the outward force of the prosthesis and the symmetrical band aligned along the annular ring. This approach is commonly used and it is acknowledged that a symmetrical sealing ring is a useful approach, which serves the purpose, however, this approach is not always 100% successful.

Yet another issue is the need for pacemaker implantation after heart valve replacement therapy. In currently available therapies and heart valve prostheses a considerable number of patients require a pacemaker implantation after heart valve replacement therapy. Currently there are a number of replacement heart valves on the market like the Sapiens HVT, the Lotus device, the Corevalve device or the Symetis device all for aortic heart valve replacement with a minimally invasive approach. The percentages of the requirement for pacemaker transplantation vary between these products. It is acknowledged that the pacemaker requirement is unwanted and makes yet another surgery necessary including all its negative implications.

Accordingly, there is a need to provide for methods and replacement heart valves with a reduced need of pacemaker implantation.

Hence it is one object to provide for a replacement heart valve therapy with reduced pacemaker rate.

It is another object to provide for a means and a method for save positioning replacement heart valves into an individual's body at a target site.

It is yet another object to be able to visually control the correct positioning of a replacement heart valve.

It is another object to provide heart valve prostheses with good or even advantageous leak tightness features.

It is yet another object to provide for a replacement heart valve therapy wherein the replacement heart valve is engineered in a manner so as to reduce or even substantially avoid the disadvantages of the prior art, or to provide for a replacement heart valve that combines the advantages of being capable of secure and correct positioning and at the same time exhibiting a reduced need for pacemaker implantation.

It is yet another object to provide for a replacement heart valve prosthesis which has improved properties or/and which exhibits advantageous features with respect to the pacemaker need, e.g., a reduced pacemaker need vis-à-vis known devices or a pacemaker rate that is acceptable, easy positioning, and/or good leak tightness features.

SUMMARY

In one aspect are disclosed replacement heart valve prostheses with the reduced need of pacemakers. The reduced need for pacemaker application after the replacement heart valve implantation according to some embodiments may be related to aspects of the prosthesis design.

In another aspect are disclosed methods for the minimally invasive application of said replacement heart valves by use of a catheter device in a transfemoral or transapical manner.

The catheter may be adapted to the prosthesis in order to allow easy and correct implantation into the heart of an individual.

In another aspect is disclosed means for visualizing the positioning of replacement heart valves at an implant site inside an individual's body, wherein the medical implant exhibits a deformable indicator means.

In another aspect is disclosed a method for the visualization of the positioning of a medical implant exhibiting deformable detector means at an implant site inside a patient body wherein i. the implant is delivered by appropriate means close to or at least relatively close to the target implantation site; ii. the implant is approached to its final target site; iii. the approach of the implant is stopped when the deformable detector means indicate contact with the tissue of the final target site.

In yet another aspect is disclosed a method for minimally invasive implantation of a replacement heart valve in an individual.

BRIEF DESCRIPTION OF THE DRAWINGS

The Figures will describe various aspects without being understood as restrictive. The skilled person will also appreciate that any of the features as described in the Figures or in any of the examples mentioned herein may be combined with any other features or a number of features as described throughout the specification and claims herein.

FIG. 2 depicts an aortic replacement valve according to an embodiment of the disclosure (14) flapped open to show three sections (16), (17), (18) from left to right and the distal prosthesis area. (9), (10), and (11) refer to the right coronary sinus, non-coronary sinus and left coronary sinus, respectively. The left coronary (12) and right coronary (13) are shown wherein the prosthesis is designed so as not to cover the coronaries (12) and (13). The prosthesis (14) in this embodiment exhibits between section (16) and (18) an area (19) which has a higher proximal edge.

FIGS. 4a-4b and 5a-5b show variations in the connection between the locator (20) and the fastening arches (23).

FIG. 6a shows an aortic valve prosthesis comprising a stent, arch-shaped locator (20) connected to the commissures and extending proximally, and an arch-shaped indicator (25) connected to the commissures and extended proximally beyond the locators (20). The indicators may be formed e.g. from flexible radiopaque wires. FIG. 6b shows a locator (20) and corresponding indicator located distal to a native cusp. The indicator (25) is in its undistorted configuration. In FIG. 6c, the locator is advanced to the base of the native cusp. The indicator contacts the cusp first and is deformed by the force used to further advance the locator (20) and stent. The locator (20) is relatively stiff and does not deform. When the locator (20) approaches the base of the cusp, the most proximal segment of the indicator and the most segment of the locator (20) approach each other and contact each other. This configuration indicates that the locators are in full contact with the cusps. The locator and the indicator are radiopaque and there physical location to each other can be visualized using fluoroscopy. Alternatively, the locators (20) and/or the indicator may be made from non-radiopaque material. Individual radiopaque markers may be placed on the proximal segments of the locator (20) and indicator to visualize their respective location using fluoroscopy.

In FIGS. 7a-7c, a series of "antennas" extend from the proximal segment of the feeler in the direction of the cusps. The antennas may be made from flexible material such as a memory alloy. The antennas may have similar properties as guide wire tips to prevent tissue damage. The tip of the antenna or the entire antenna may be radiopaque. When the antennas contact the cusp (27) they are deflected. When multiple antennas are used, the array of antenna tips outlines the shape of the cusps (27). This may be helpful in visualizing the center of the cusp (27).

FIGS. 8a-8c show another alternative embodiment of the locators (20) and indicators (25). Each locator has an "M" shape with the ends of the M being connected to the stent. The center "Y" segment of the locator sits inside the valve cusp sandwiching the cusp between the Y segment and the stent. A single indicator (25) is connected to the base of the Y shaped locator (20) segment. The indicator may be similar in shape and construction of the indicators in FIGS. 7a-7c. Alternatively, the indicator (25) may be made from soft fabric, textile, mammalian tissue, or a polymer. Polymers may include but not limited to silicone, polyurethane, and ePTFE. The fabric, textile, and mammalian tissue may be attached to the locators (20) by sutures, clips, staples, or adhesives. The polymer may be attached to the locators (20) by adhesives, heat fusion, or over-molding. At least the proximal end of the indicator (25) may be radiopaque. Radiopaque markers may be sewed onto the fabric or imbedded or molded into the polymer material. the implantation direction into the cusps (27) is indicated by arrow (26).

FIG. 9 illustrates a indicator in form of a locator cover (28) which is affixed to the locator (20) and comprises one or more radio-opaque means for visualization with respective means and methods known by the skilled person during surgery. The locator cover (28) can be cut in different forms and seizes as is appropriate for affixing same to the locator (20). Such a cover may be made of material compatible with the remaining components of the prosthesis and may exhibit biocompatible characteristics. The cover (28) may be well compatible with its function and long term implantation into an individual. The cover and as well the other components of the prosthesis such as stent, biological and non-biological materials can be covered or coated with a coating which may facilitate implantation and/or biocompatibility with the tissue of the implantation site in the heart. The FIGS. 9a, 9b, 9c illustrate variations in the cover (28) and the positioning of the radio-opaque markers (29).

DETAILED DESCRIPTION

Figure 1C:
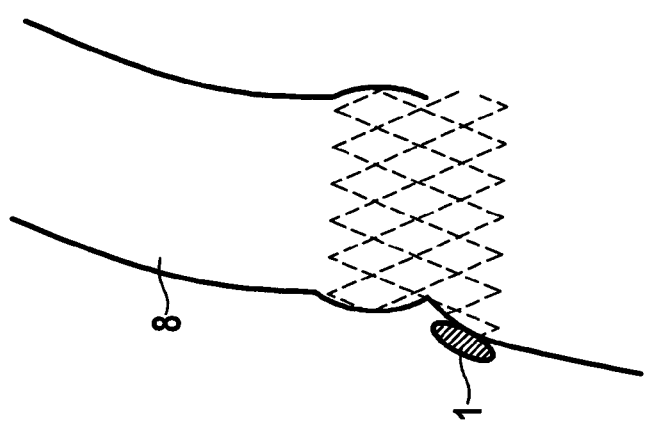
FIGS. 1a-1c, at the left side, (FIG. 1a) describe a top view of a heart with the bundle of His (1), the septum (2), the mitral valve (3), the aortic valve with right leaflet (4), left leaflet (LC) and non-coronary leaflet (6). In the middle (FIG. 1b) is depicted the annular ring (7) of the aortic valve and the aortic arch (8). On the right side (FIG. 1c) a prosthesis is placed at the site of the endogenous aortic heart valve in the annular ring (7).

The objects of the disclosure may be addressed by the prostheses and methods as disclosed herein.

In the following some terms of the disclosure will be defined and unless stated otherwise they will represent the meaning for the purpose of the description of the subject matter described herein.

"Heart valve prosthesis" or "prosthesis" or "medical implant" or "medical device" in the sense of the disclosure is any medical device like a heart valve that may be implanted into a patient by means of a minimally invasive procedure e.g. by way of the use of a catheter or a similar delivery device. "Prosthesis" relates to aortic, mitral and tricuspid replacement heart valves.

The term "proximal" refers to the part of the prosthesis which will be closer to the apex of the heart during or when implanted, and the term "distal" refers to the part of the prosthesis which is further away from the apex of the heart during or when implanted. The term "proximal" may also be used in the context of the locator means.

The term "varying" in connection with the proximal end or the edge of the proximal end refers to the specific design of the disclosed subject matter, wherein the edge of the proximal end of the prosthesis can be uniform and describe a ring ending at the same level. On the other hand different sections of the prosthesis can be designed in a way so as to have their edges of the proximal ends at differing levels and thus represent differing distances to e.g. the locator means in case the prosthesis consists of three sections wherein each section comprises on locator means. Thus the proximal end of the prosthesis may exhibit an undulating proximal edge.

"Tube perimeter" refers to e.g. a nitinol tube which is laser cut in order to receive the stent component of the prosthesis and which describes the same inner and outer dimension and surface over the tube. Accordingly, in some embodiments, no parts of the cut stent may substantially stick inwardly or outwardly of said tube.

The term "foreshortening" describes the change of position or position of the proximal end of the locator means when the stent component is expanded and the proximal end of the locator means moves outwardly of the tube perimeter and towards the proximal end of the prosthesis. Thus the distance between the proximal end of the locator means and the proximal end of the stent may be reduced "shortened" as compared to the non-expanded position of the proximal end of the locator means. The "foreshortening" may depend on the design of the locator means as such and on the connection with other parts of the stent. Thus a design such as an arch may be advantageous and its connections with its ends at each side with a fastening arch of the stent. The skilled person will appreciate that in this manner the "foreshortening" can be defined and it can vary between 1 and 15 mm, or one can achieve a foreshortening of 1, 2, 3, 4, 5, 6, 7, 8, 9, 10, 11, 12, 13, 14, or 15 mm.

A "fastening arch" is a part of the stent to which the valve component is fixed, e.g., by suitable means and methods.

A "non-expanded state" and "expanded state" of the prosthesis refers to a design wherein the prosthesis can be crimped and placed to or in a catheter for minimally invasive delivery purposes. The prosthesis may be expanded by balloon expansion or self-expandable, and when placed and positioned at its target site it may exhibit its "expanded state". Thus the "non-expanded state" represents the minimal diameter of the prosthesis and the "expanded state" represents its biggest diameter. It will be appreciated by the skilled person that the prosthesis when positioned at its target site may exhibit outward forces against e.g. the annular ring which may exhibit a force in counter direction and thus the prosthesis may not exhibit in this state its maximal diameter. The outward force may contribute to the fixation/positioning of the prosthesis.

"Heart pacemaker" or "pacemaker" in the sense of the disclosure are devices to trigger and control an appropriate or normal heart rate in an individual.

"Pacemaker rate" or the "need for pacemaker" or "the need for pacemaker implantation" relates to the fact that in heart valve replacement therapy after implantation of the prosthesis a number of patients require pacemakers.

Accordingly, an additional surgery is required in such individuals.

"Pacemaker rate" in this context refers to the percentage of individuals who need a pacemaker after valve implant. The pacemaker rate in currently available replacement heart valve treatment is in the range of 10% to 30%.

"Indicator means" or "indicators" in the sense of the disclosure are any constructive means that allow or facilitate the easy and precise positioning, e.g., by way of a visualization apparatus or devices that allow controlling the position of the medical device within a patient.

"Locator means" or "locator" or "feeler" in the sense of the disclosure is to be understood as any constructive element as part of the medical device to be implanted in an individual and which allows or facilitates the implantation and positioning, e.g., by making contact with or within a body or tissue part of the individual. The locator may be designed as is appropriate under the circumstances which will be described in more detail below.

"Locator probe" may form part of or be used together with a locator means and it may facilitate the correct positioning of the prosthesis at the target site in the individual. For easier visualization a opaque marker may be used.

A "valve component" in the sense of the disclosure is a biological or synthetic valve placed within the stent component and which may replace the endogenous valve function. It may comprise additional components to optimize the valve and overall prosthesis function, including, by not limited to, internal and/or external covers of the same or different biological and/or synthetic materials and sealing means.

A "sealing means" in the sense of the disclosure is a particular tissue, lining, covering, band made of synthetic and/or biological material that may be positioned outside the stent component, e.g., which may serve the purpose to prevent reflux of blood when the valve is in its closed position. In some embodiments, it is designed as a band around the stent component in e.g. an aortic valve as a symmetrical band at the location of the annular ring and which represents a sealing between the prosthesis and the endogenous valve. The "sealing means" of the disclosed prosthesis may be symmetrical and/or non-symmetrical and it may follow in particular at the outside of the prosthesis and may represent a covering. In a non-symmetrical design of the prosthesis as disclosed the "sealing means" may be more distal in the NCS section and more distal in the other two sections (16) (18).

The "target site" in the sense of the disclosure is the endogenous heart valve to be replaced by the replacement heart valve. In particular the "target site" is the position where the replacement heart valve will be implanted.

"Shortest distance" in the sense of the disclosure refers to two points that relate to design features of the prosthesis like locator and distal end which can be compared to the distance of other design features wherein the distance is measured in the same manner. "Opaque marker" in the sense of the disclosure is to be understood as any material that can be visualized by an apparatus to visualize the position of the device outside the individual's body during surgery or thereafter.

"Visualization" or "to visualize" in the sense of the disclosure includes any way to project the opaque marker and thus prosthesis position outside the individual's body.

Any other terms used in the following will be understood by the skilled person in the art and in the usual sense and manner usually applied in the art.

In the following various embodiments will be described wherein the skilled reader will understand that all features described therein may represent one single feature of the prosthesis and/or all features of the prosthesis, and any features as described herein may as well be combined in any way even if not explicitly so mentioned in the following.

Figure 1B:
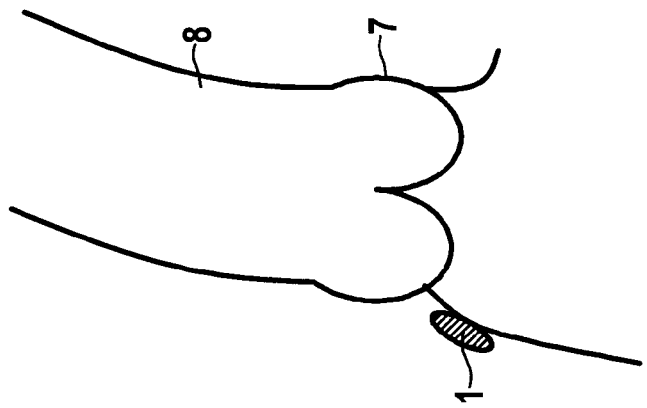
Figure 1A:
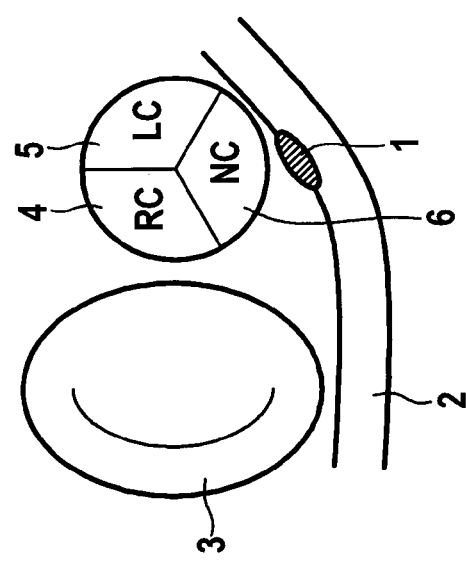
Figure 3:
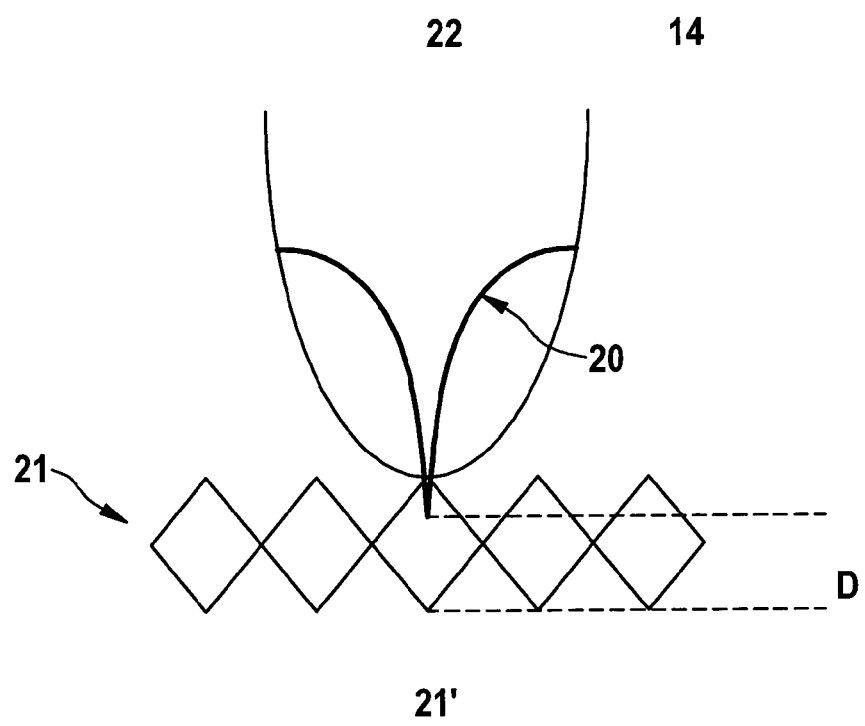
FIG. 3 illustrates a part of the prosthesis according to another exemplary embodiment of the disclosure (14) wherein particular aspects of the stent forming part of the prosthesis are depicted. Other parts as necessary may form part of a prosthesis of the present disclosure which are not explicitly shown but which may form part of the prosthesis as disclosed herein. In particular the locator (20) and the proximal stent ring (21) are depicted. The proximal end of locator (20) may be specifically designed and engineered to provide for a particular dimension and distance with regard to the proximal end of the prosthesis according to the disclosure (14). In the present illustration it is 6 mm. However, other dimensions can be useful depending on the particular needs and requirements which can be adapted to, such as, e.g., a range of between 1 and 10 mm, e.g. 4 mm, 5 mm, 7 mm, 8 mm.
Figures 4A, 4B:
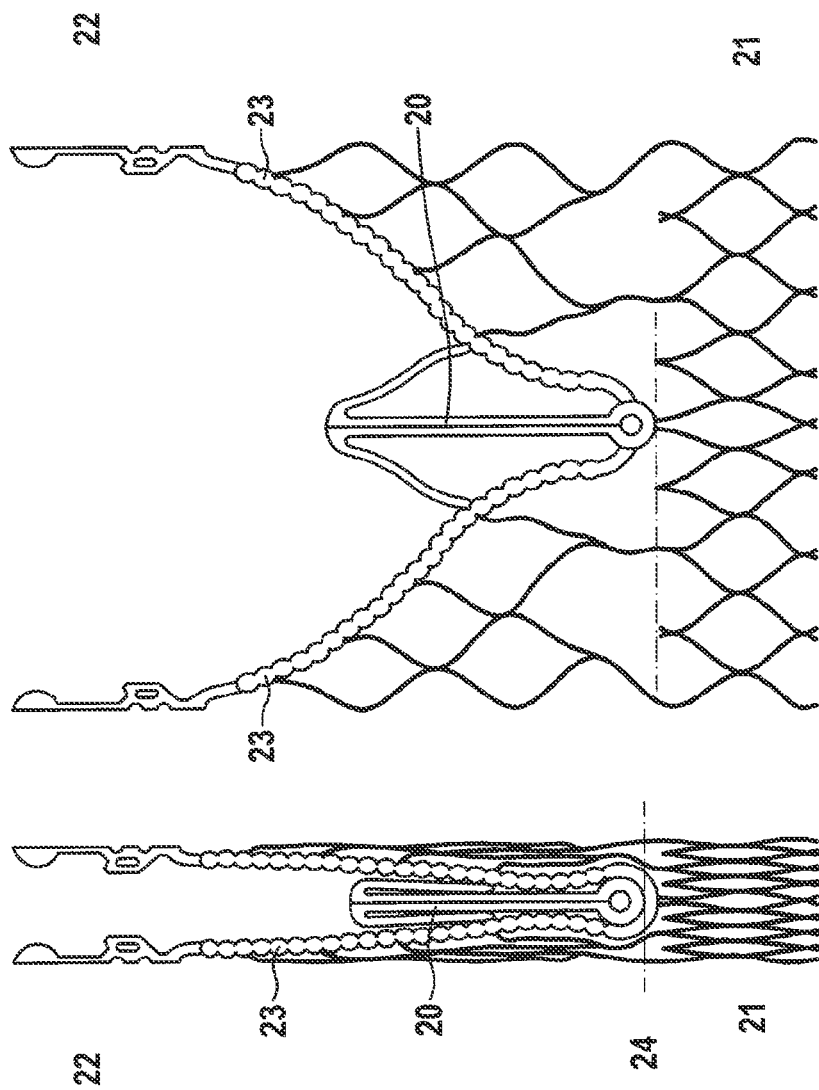
Figure 6C:
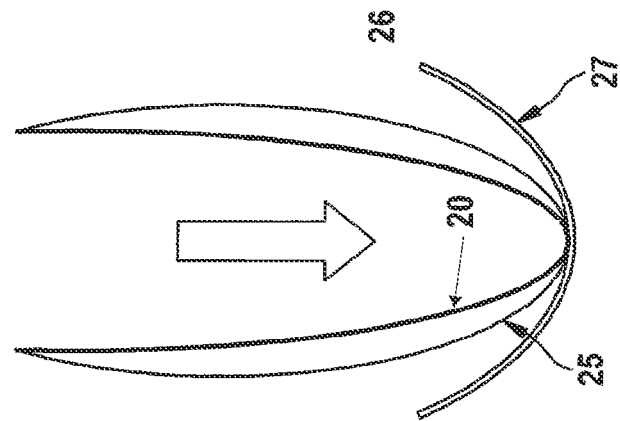
FIGS. 6a-6c show a prosthesis (14) according to another exemplary embodiment of the disclosure exhibiting a feeler and an indicator, and wherein the sequence of positioning of a medical implant according to the present disclosure is depicted.
Figure 6B:
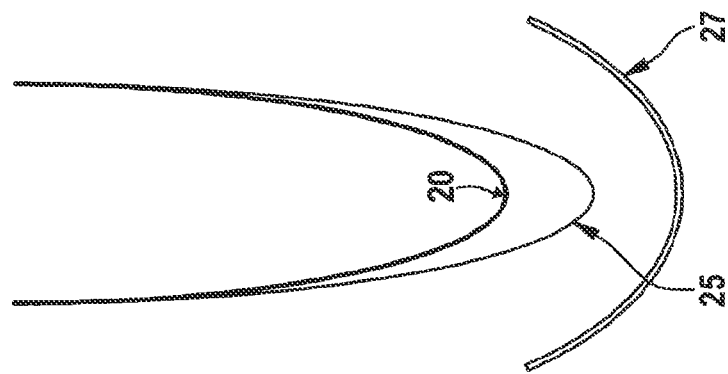
Figure 6A:
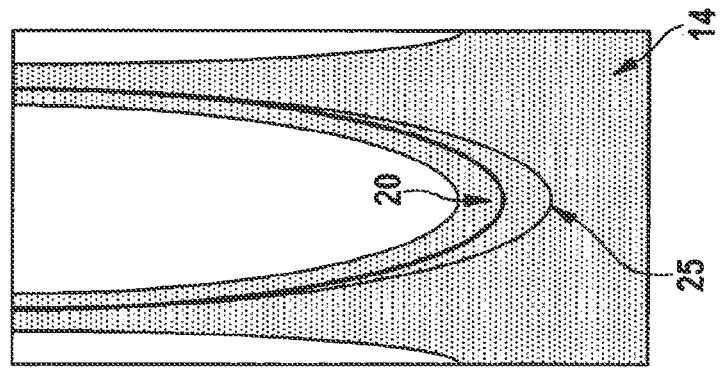
Figure 7C:
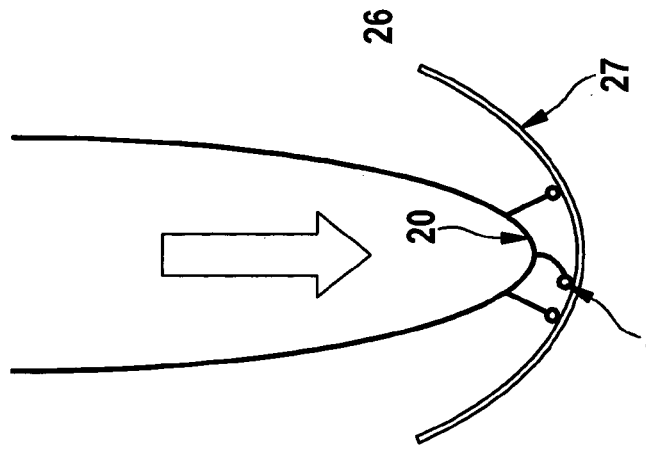
FIGS. 7a-7c and 8a-8c show alternative embodiments of the locators (20) and radiopaque indicators (25).
Figure 7B:
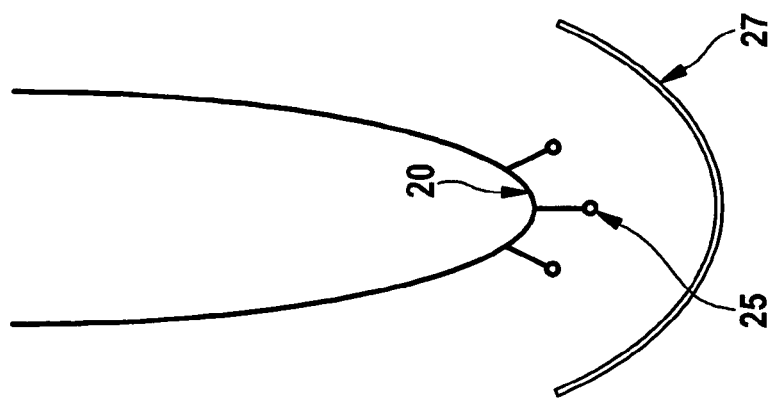
Figure 7A:
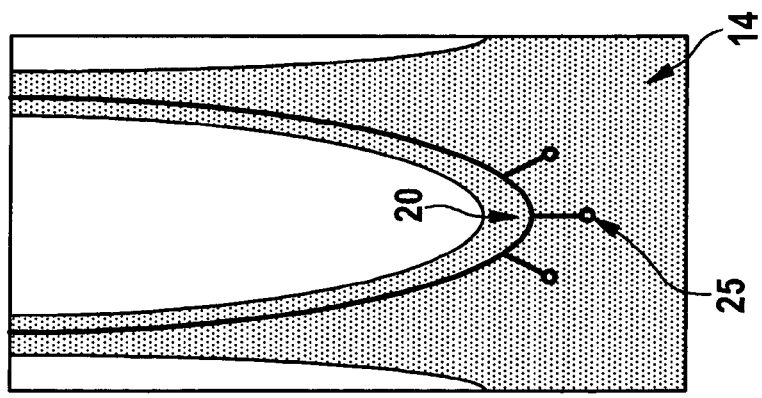
Figure 8C:
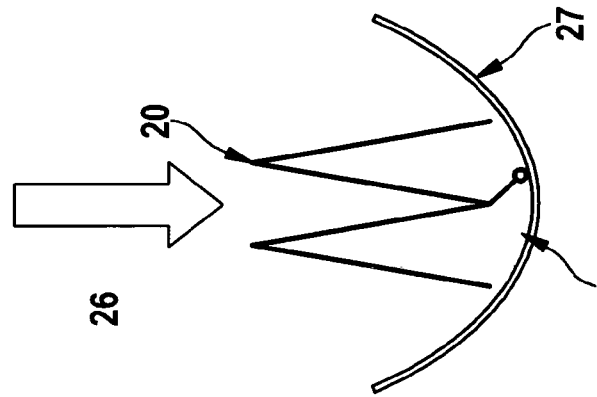
Figure 8B:
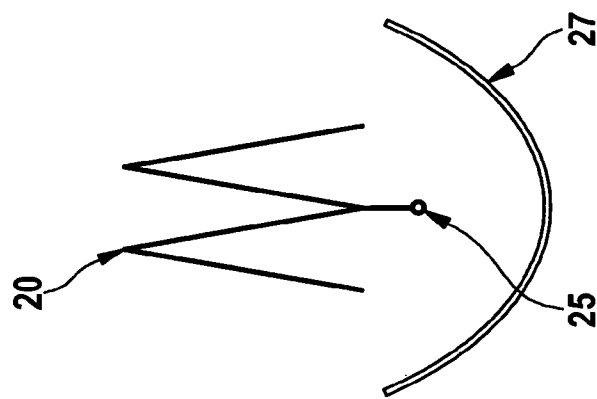
Figure 8A:
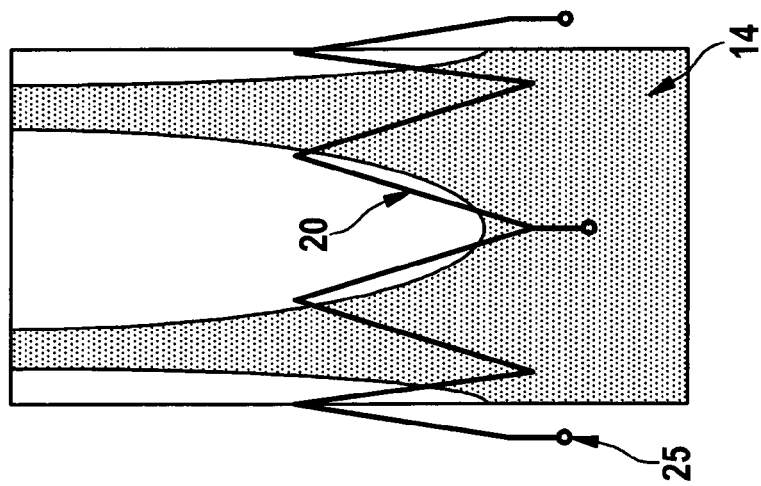
Figure 10A:
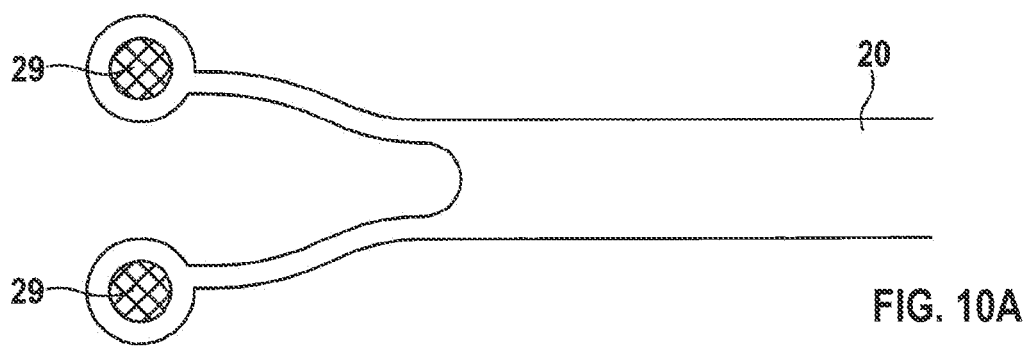
FIGS. 10a-10c show variations of locators (20) including a radio-opaque markers (29) wherein the locators (20) as well as the markers (29) are engineered with variations and additional variations in seize, dimension, marker (29) location are well within the scope of the present disclosure.
Figure 10B:
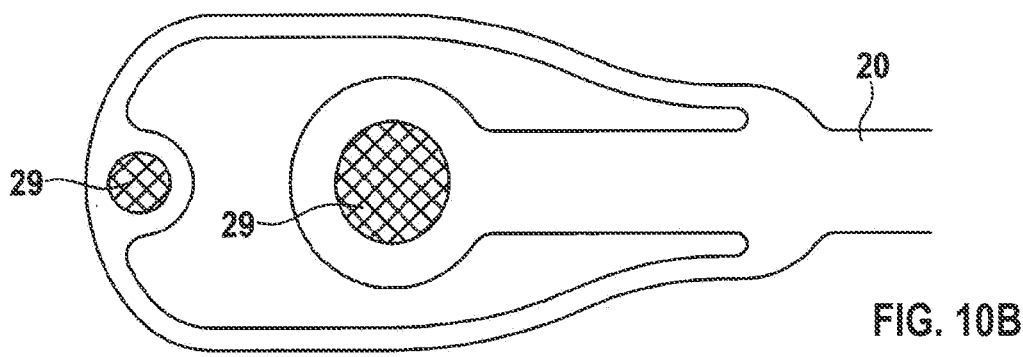
Figure 10C:
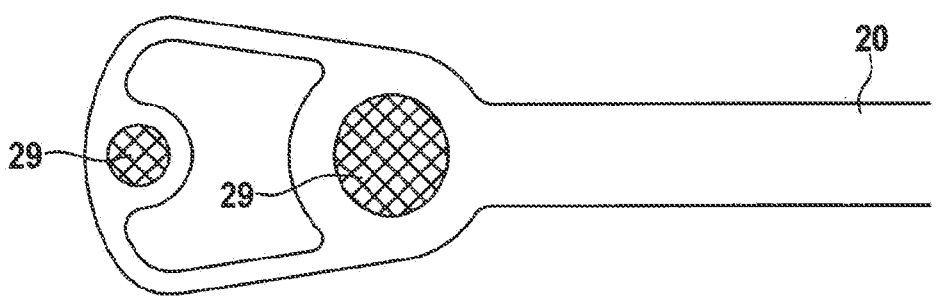
Figure 11:
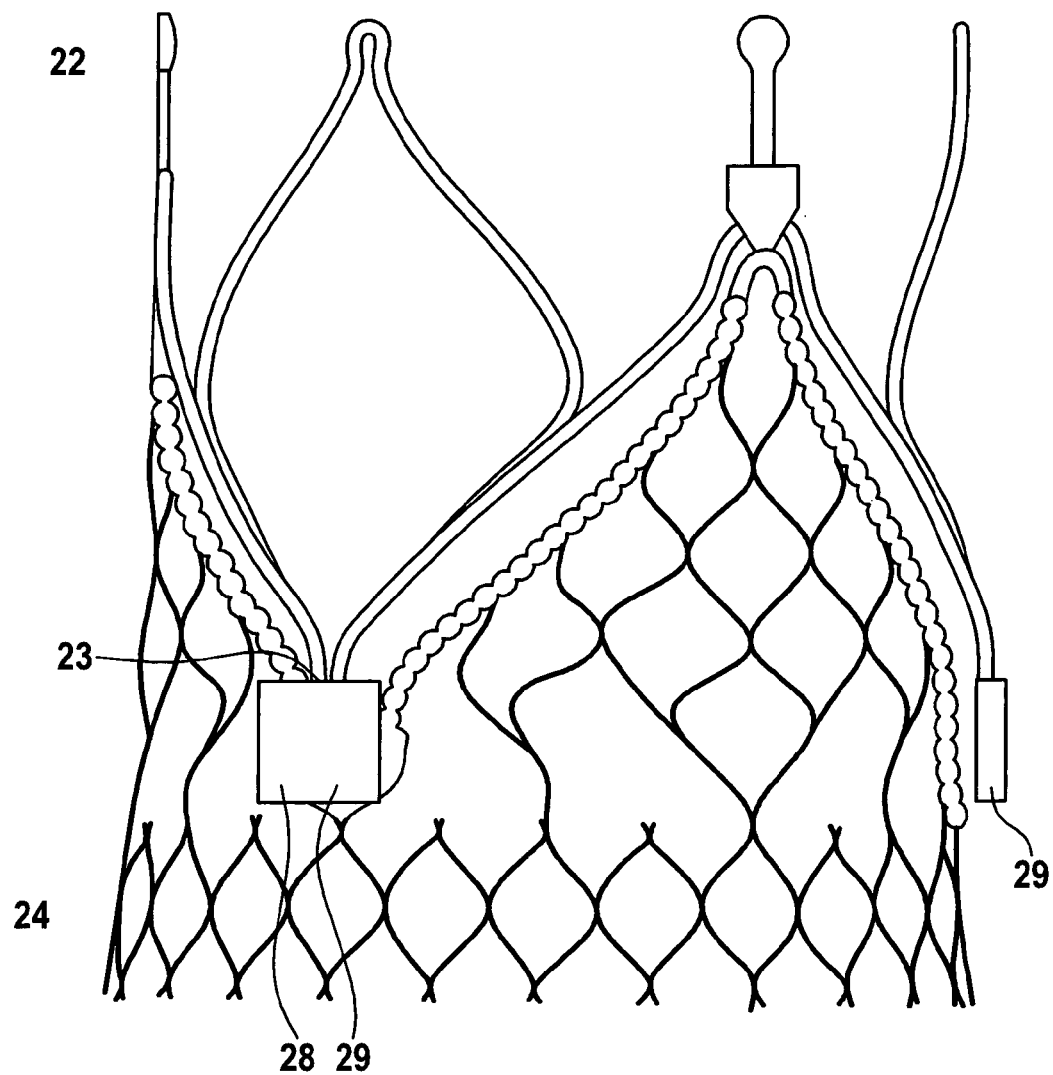
FIG. 11 depicts a prosthesis (14) according to an exemplary embodiment of the present disclosure and illustrates the cover (28) including the radio-opaque marker areas (29) attached to a locator (20) and indicates the distal area (22), the proximal area (24), the fixation arches (23).
Figure 12:
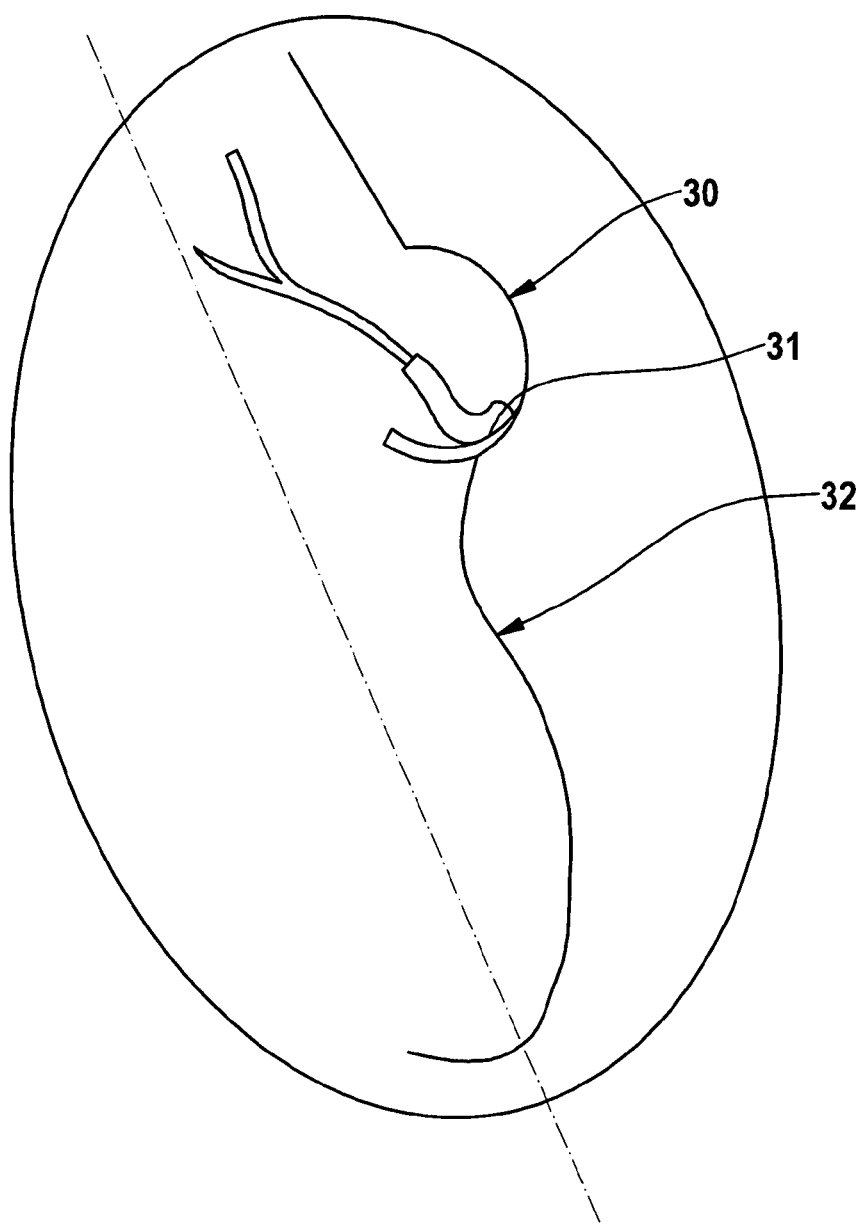
FIG. 12 shows the prosthesis (14) implanted at the aortic annulus ring and the use for facilitation of better positioning by way of the locators (20) and radio-opaque (29) marked indicator in form of a locator cover (28) wherein calcified leaflets (31), the sinus of vasalva (30) and the (32) are shown.
Figure 13C:
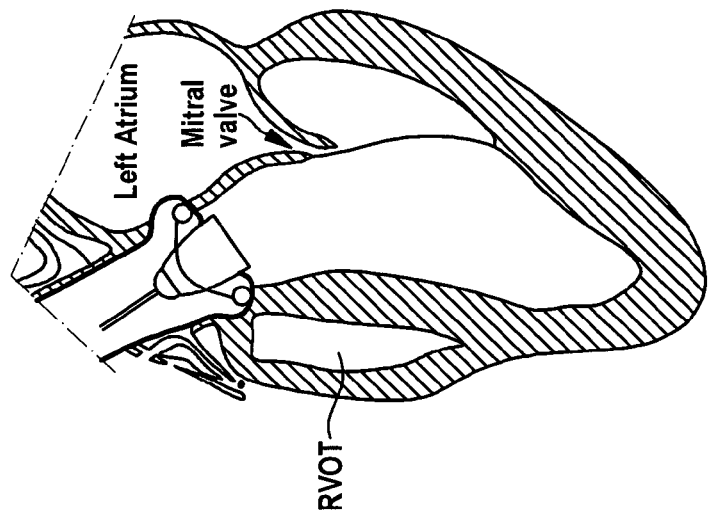
FIGS. 13a-13c show another way of illustrating the prosthesis (14) as of FIG. 12 positioned and implanted at its target site.
Figure 13B:
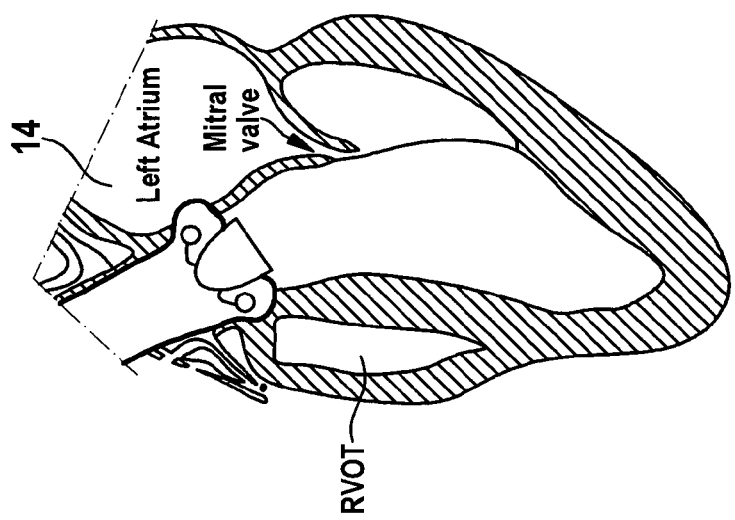
Figure 13A:
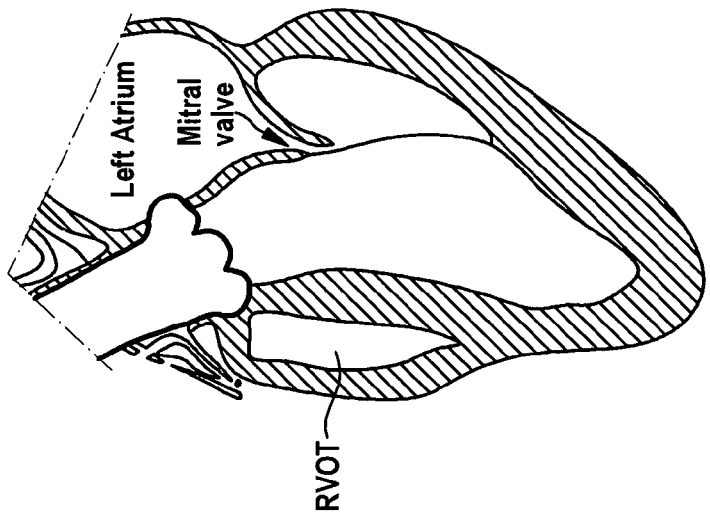
Figure 4B:
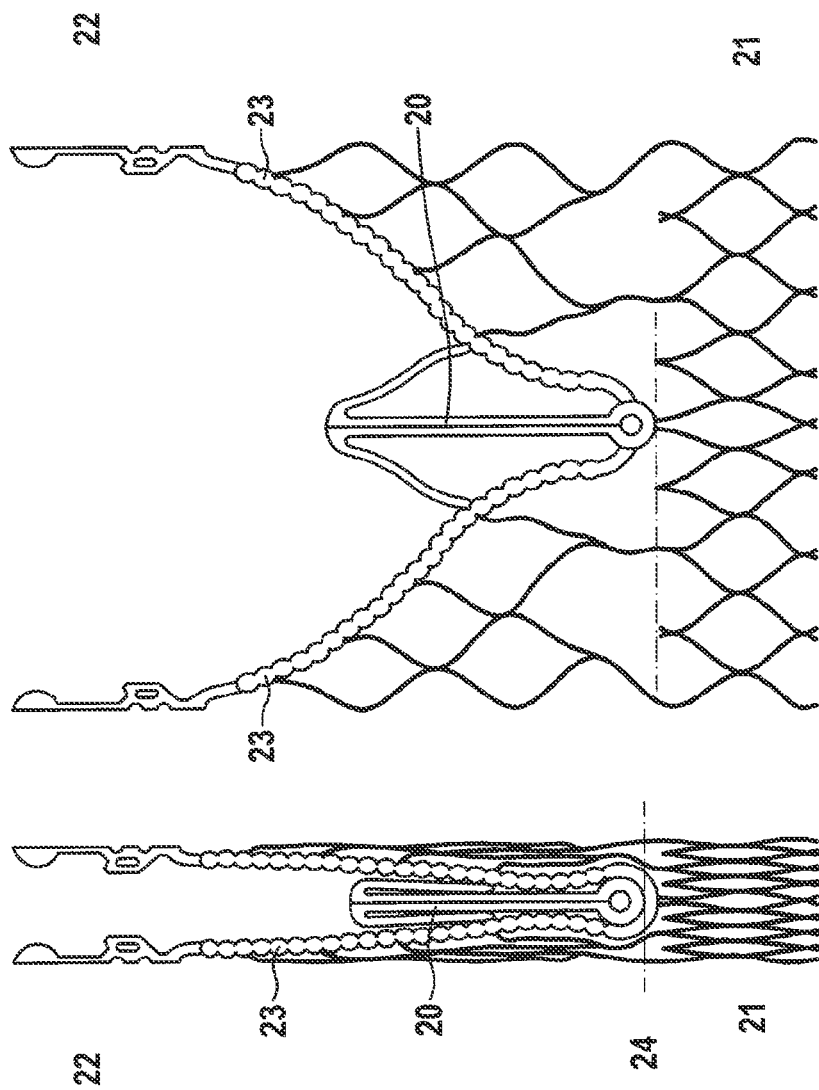
Figure 4A:
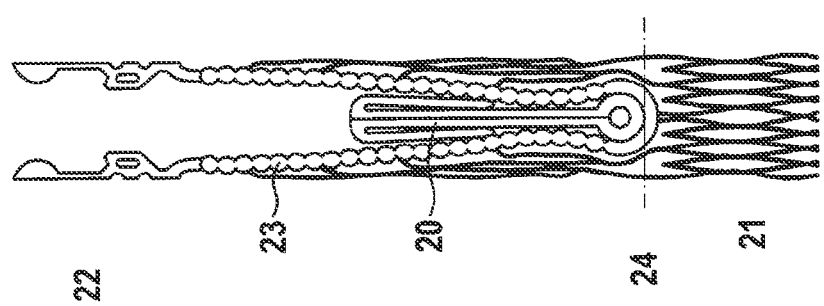
FIG. 4a (non-expanded state) and FIG. 4b (expanded state) show a prosthesis according to an exemplary embodiment (14) with a locator (20) attached to fastening arches (23). Also indicated are the proximal and distal prosthesis areas (21) and (22), respectively. The locator (20) may have an adapted design and positioning with respect to and as being connected with fastening arches (23). Also indicated is the foreshortening distance (24) and the fact that in its expanded state the locator(s) (20) may at least partially superpose some areas of the remaining prosthesis. The prosthesis (4) may exhibit three locators (20) but it may also be feasible to use more or less locators, e.g. two locators. Also the locators (20) may have the same design and length or may represent different embodiments, e.g., being engineered differently.
Figure 5B:
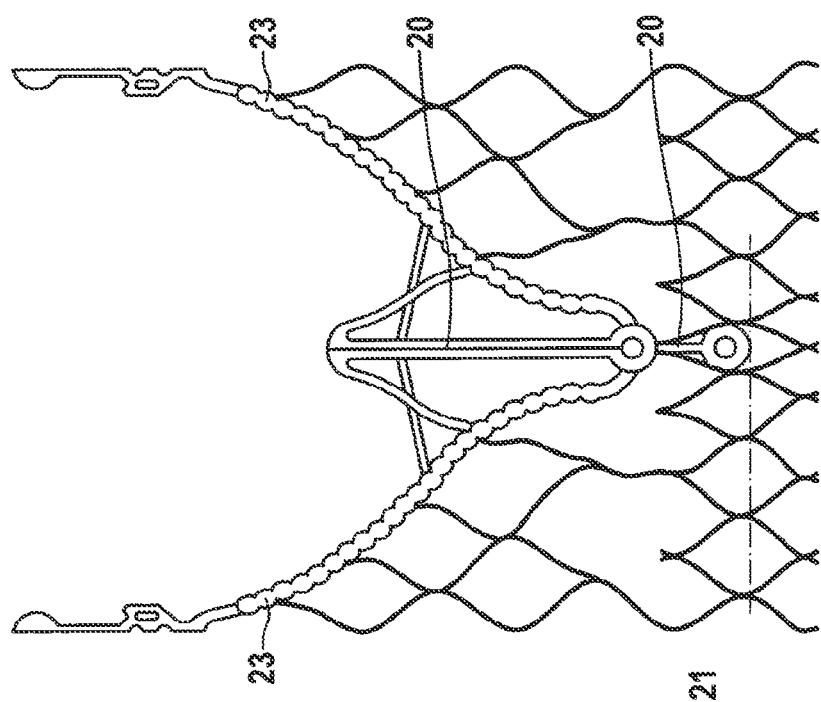
FIGS. 5a-5b show a variation of the prosthesis of FIGS. 4a-4b wherein the locator (20) is differently engineered and the foreshortening distance (24) is achieved in a variation of the one depicted in FIGS. 4a-4b.
Figure 5A:
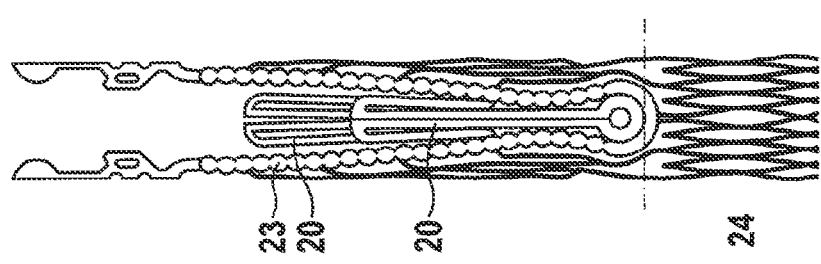
Figure 10A:
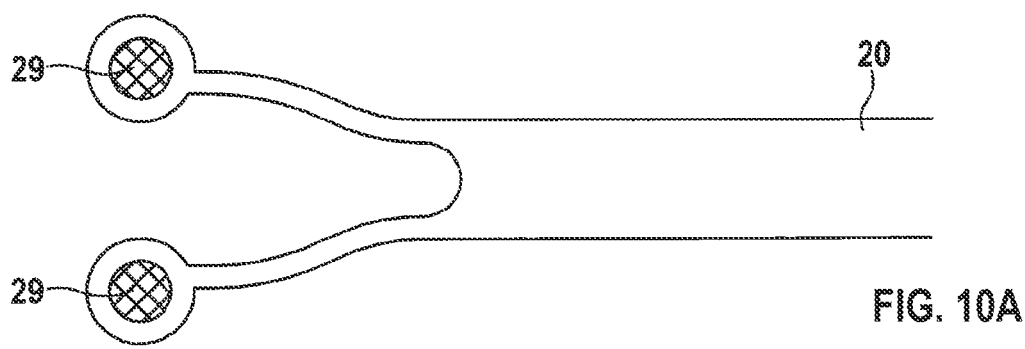
Figure 10B:
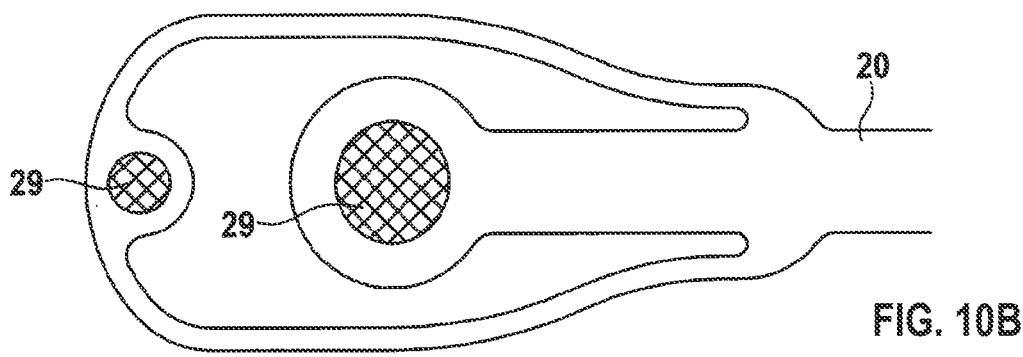
Figure 10C:
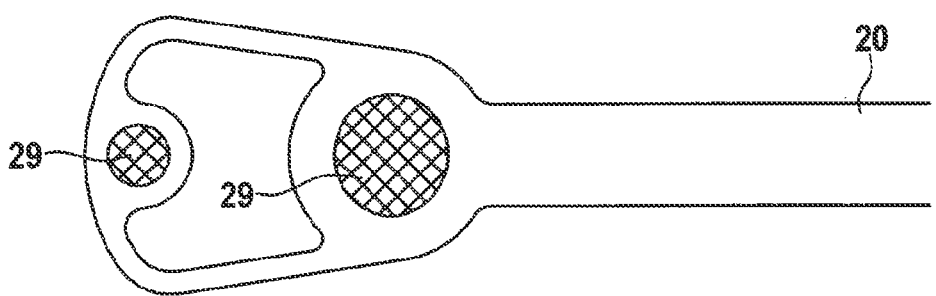

In one aspect the disclosure relates to an aortic heart valve prosthesis for reducing the need for pacemaker implantation. FIG. 1 illustrates the anatomical location of the bundle of His of the conductive system. The bundle of His is located at the septum approximately 2 mm-10 mm below the aortic annulus and the non-coronary sinus. Many transcatheter prostheses for aortic valve replacement include a balloon or self-expanded stent scaffold that anchors the prosthesis in the aortic annulus. There is evidence that the stent scaffold interferes with the conductive system of the heart, which may result in the need for pacemaker implantation. A stent scaffold that extends into the left ventricle or excessively stretches the tissue in the aortic annulus may injure or irritate the bundle of His.

One potential strategy to mitigate the risk of irritating the conductive system is to place the proximal end of the stent scaffold within the aortic annulus and avoid extension of the stent scaffold into the left ventricle. This may require accurate axial placement of the stent scaffold inside the annulus. In one aspect of the present disclosure, the stent scaffold of the valve prosthesis includes axially extending locators. The locators may be positioned within the cusp of the native aortic valve. Placement of the locators within the cusps may prevent further proximal movement of the stent scaffold into the left ventricle. By adjusting the location of the proximal end of the locators with respect to the proximal end of the stent scaffold, infra-annular placement of the stent scaffold in the aortic annulus may be assured. The distance from the proximal end of the locators to the proximal end of the stent scaffold may be less than 10 mm, for example between 1 mm-5 mm.

The location of the proximal end of the locators with respect to the proximal stent scaffold may require the locators to overlap with the proximal stent ring of the stent scaffold. In an exemplary embodiment, the locators and the stent scaffold of the prosthesis are cut from the same metal tubing. This may minimize the profile of the prosthesis. FIGS. 4*a*-4*b* and 5*a*-5*b* demonstrate embodiments of one-piece stent scaffolds with locators. The locators may be connected to the mid-section of the stent by diagonal struts. Expansion of the stent scaffold from the crimped configuration into the implant configuration may cause foreshortening of the diagonal struts and proximal movement of the proximal end of the locators. In the crimped configuration, the proximal end of the locators may not overlap with the most proximal stent scaffold ring. In this configuration, the stent scaffold may have a low profile for placement in the delivery system. In the expanded configuration, the proximal end of the locators may overlap with the most proximal stent scaffold ring. In some embodiments, the proximal end of the locators is located less than 10 mm, e.g., between 1 mm and 5 mm, away from the proximal end of the stent scaffold when the stent scaffold is fully expanded.

In another aspect of the disclosure, interference of the stent scaffold with the bundle of His may be mitigated by an asymmetric stent scaffold design. The most proximal segment of the stent scaffold along the non-coronary sinus may be moved distally with respect to the most proximal segments of the stent scaffold along the left and right coronary sinus. The most proximal segment of the stent scaffold along the coronary sinus may be within or supra to the aortic annulus. In conjunction with the more distal placement of the non-coronary segment of the stent scaffold, the paravalvular seal zone in the non-coronary segment of the prosthesis may extend into the non-coronary sinus. Distal extension of the seal zone may be possible since the non-coronary sinus is void of coronary arteries that need to be kept patent to perfuse the heart. Thus, an asymmetric design of the prosthesis may take advantage of the unique anatomical location of the bundle of His with respect to the annulus and the non-coronary sinus. The seal elements of the prosthesis may be located proximal to the coronary arteries in the left and right coronary sinus and distal to the coronary arteries in the non-coronary sinus.

In another aspect of the disclosure, the prosthesis may have an asymmetric design and two locators for placement in the right and left coronary cusps. The non-coronary segment of the stent scaffold may not have a locator but a supra-annular stent segment that contacts the wall of the non-coronary sinus.

In one aspect the disclosure relates to a heart valve prosthesis for reducing the need for pacemaker after positioning at a target site, comprising a stent component, a valve component, a sealing means, and at least one locator means for a defined positioning of the prosthesis at the target site of an endogenous heart valve, and wherein the prosthesis may be expandable from a non-expanded to an expanded state, and wherein in the expanded state a shortest distance between a proximal end of the locator means and a proximal end of the prosthesis may be less than 15 mm, such as less than 10, 8, or 5 mm.

The prosthesis as disclosed herein may exhibit a number of advantages compared to other devices at least partially due to its engineering. For example, one advantage may be that the design of the prosthesis makes sure that the coronary arteries are substantially not covered or blinded by any prosthesis section or area and thus the circulation of blood is not affected.

Another advantage of the prosthesis as disclosed may be that its implantation may not substantially interfere with the heart functions. For example, its implantation may result in low side effects, e.g., such that the rate of pacemakers needed may be comparably low as compared to other devices.

In one embodiment the heart valve prosthesis as disclosed comprises a locator means comprising a locator probe for the visualization of the locator means.

The prosthesis can be a tube and/or mesh like design with symmetrical end portions. It can as well have in its structure within the tube structure asymmetrical with meander like structures and it can as well be designed so that the distance between a proximal end of the locator means in case there are two or three locator means referring to the three sections as described herein and a proximal end of the prosthesis is varying in circumferential direction. The same is possible for the distal end of the prosthesis. Such a design may be suitable, for example, wherein the proximal and/or distal end is varying in its end dimensions. Such a design may provide an advantage wherein critical areas and/or various other areas of the heart may be kept without contact with the prosthesis, or the contact may be minimal or such areas of the heart even repeatedly with or without contact with the prosthesis. Thus, in some embodiments, the disclosure may allow for the respective functional areas of the heart to exhibit without interference its functions. Examples may include the coronary arteries and the bundle of His.

The prosthesis as disclosed herein in one aspect may be designed wherein in the non-expanded state the locator means and the stent component extend along a tube perimeter and in the expanded state the locator means extend at least partially outside an expanded tube perimeter.

In a prosthesis as disclosed herein which exhibits locator means in one aspect may be characterized in that in the expanded state the locator means is positioned in proximal direction at least partially over the remaining stent portion (e.g., foreshortening).

The foreshortening may allow for a design—possibly in combination with one or more other dimensions of the prosthesis—which finally allows for a precise and correct positioning of the prosthesis at the target site and may reduce—possibly together with one or more other design features of the prosthesis as disclosed herein—the need for pacemaker implantation.

In an exemplary embodiment the foreshortening of the locator means in the expanded state compared to the non-expanded state is 1, 2, 3, 4, or 5 mm. The foreshortening can be adapted in particular prosthesis seizes, e.g. 23, 25 or 27 French, as may be useful in connection with the other prosthesis design features and seizes and dimensions. In such a manner the positive effect of reduced pacemaker need may be optimized as will be appreciated by the skilled person.

The locator means may be made as a locator arch and may be attached to or forming an integral part of the stent component. In some embodiments, the prosthesis may contain three locator means, each one being positioned in one section of the prosthesis. It may as well be designed in other geometrical forms.

The locator arch may be attached or forming an integral part with each of its ends with one fastening arch of the prosthesis. When the prosthesis expands from is non-expanded to its expanded stage at least two fastening arches, e.g., six fastening arches, two in each of the three prosthesis sections and three locator means respectively, may separate from each other and the locator arch may move with its tip in direction to the proximal end of the prosthesis. In this manner the positioning of the prosthesis and the dimensions of cusp positioning of the locator means, which may be one, two or three, and the proximal end within the target site (i.e. the endogenous heart valve) may be defined as well as the distances between the locator means ends as well as the proximal end of the prosthesis.

In one embodiment the fastening arch comprises fastening means which may serve for adjusting the valve component on the stent component. Other components like covers inside and/or outside the stent component made from biological or synthetic materials may also form part of the prosthesis as desired. Such covers may serve as sealing means.

In one embodiment the prosthesis as described herein is designed in a manner to substantially not cover the coronary arteries in the expanded state when placed at the target site. Thus the stent and covering components may be designed so that the respective parts are not at all covered, or exhibit one or more indentations provide for no or less or repeatedly no contact in line with the repeating heart beat of the individual. In such a design advantageously the respective functional areas of the heart may perform their functions without that the implanted prosthesis interferes therewith.

In one embodiment the prosthesis as disclosed herein is exhibiting or can be structured in three sections and wherein one section corresponds to the right coronary sinus (RCS), a second section corresponds to the left coronary sinus (LCS) and a third section corresponds to the non-coronary coronary sinus (NCS). The prosthesis as disclosed herein can further exhibit in one embodiment the sections wherein the three sections each comprise a distal and a proximal end, and said proximal ends extend with an equal length so that the sections RCS, LCS, NCS end at the same level, or the proximal ends corresponding to the RCS and LCS sections are shorter than the NCS section.

Accordingly, in the first above alternative the end of the prosthesis in combination with the dimensions as chosen for the locator means lead to a proximal end of the prosthesis that enters the left ventricle beyond the annular ring with less than 10 mm, such as less than 5 mm. The design of the disclosed prosthesis may provide that the heart functions are not or only minimally interfered with. In the second above alternative the prosthesis may exhibit a shortened NCS section at the proximal end and thus may avoid contact with the bundle of His.

In a third alternative the prosthesis as disclosed herein may be characterized in that the three proximal sections extend with an equal length so that the sections RCS, LCS, NCS end at the same level within the left ventricle and at the same time the NCS proximal section comprises an indentation. The indentation may provide also a design feature that avoids interference of the prosthesis with the endogenous heart functions such as inter alia a regulated and repeated heart beat.

Thus all three alternative designs of the prosthesis as disclosed herein may provide for a heart valve replacement therapy with less interference of the implanted prosthesis with the endogenous heart functions and may provide for inter alia a reduced need of pacemaker implantation.

The prosthesis as disclosed herein may achieve positive and advantageous pacemaker rates, e.g., depending on the particular design features. The prosthesis as disclosed herein after implantation in an individual may thus achieve positive pacemaker rates and may induce the need for pacemaker implantation of less than 15%, such as less than 10%, e.g., less than 8%. that the present disclosure includes a replacement heart valve prosthesis design wherein the proximal end of the proximal three sections has a shorter section NCS (17) (thus having a non-symmetrical overall design) and a non-symmetrical sealing means, which performs a good valve function and at the same time exhibits a sufficiently good sealing function and provides for a reduced need of pacemaker implantation.

In such an embodiment the sealing means may have a wave-like or U- or inverted V-shape and the sealing function may be achieved in the sections 16 and 18 at a more proximal and in the section 17 at a more distal area of the prosthesis. The areas which connect or lay between the actual sections 16, 17, 18 may be sufficient to provide for a sufficient and good sealing function.

The sealing means and sealing function may be equally designed and achieved as described above in the exemplary embodiment with an indentation area as described herein.

In another embodiment the prosthesis as disclosed may comprise a means for visualizing the positioning of the prosthesis at a target site of an individual wherein the means consists of or comprises a deformable indicator means.

The indicator means may be adapted to the other components of the prosthesis and can be adapted in any manner so that it can exhibit its function. In a embodiment the indicator means may comprise or consist of one or more wires or antennas. For visualization the indicator means may comprise radiopaque material.

In an alternative embodiment the prosthesis as described herein may comprise a counterpart to the indicator means suitable to contact each other. This counterpart may be designed in any suitable manner, and wherein the counterpart may be a locator means, a feeler, a cusp positioner, a hook and/or a rim, such as wherein the locator means, feeler, cusp positioner, hook and/or rim has U, V, Y, M or W shape.

The prosthesis as described herein may be characterized in that the indicator means and the locator means, feeler, cusp positioner, hook and/or rim may comprise the same or different materials. In one embodiment also the counterpart may comprise radiopaque material.

In at least one embodiment, a feeler means or the like may form part of the prosthesis. In one embodiment the indicator means and the feeler means or the like for a visualization means both may produce a visualizable signal. Accordingly, the operator may recognize the two signals produced by the indicator and feeler means, e.g., when the prosthesis has not reached the appropriate position. When the feeler(s), e.g., three feelers, have reached the correct position within the valve cusps the contact of the indicator means with the cusp bottom may effect a change of the geometry of the indicator means and the indicator means and the feelers may be in close proximity or in contact with each other so that the two visual signals may unify to produce at least partially at the indicator and feeler means one single signal. When the prosthesis thus has reached the correct position in the context of an aortic heart valve replacement procedure the feeler(s), e.g., the three feelers, and indicator means may be located in the cusps of the endogenous valve cusps and may produce three instead of six visual signals readily visible by the operator by way of suitable visualization means. Accordingly, the prosthesis may be positioned and its positioning can be controlled easily and efficiently.

The prosthesis as described may comprise and be made of various materials suitable for heart valve prostheses, which may consist of or comprise nitinol, soft fabric, textile, mammalian tissue, or one or more polymers, such as silicone, polyurethane, or ePTFE.

The prosthesis as described herein may be capable of replacement of any endogenous heart valve. In particular it may be useful for the replacement therapy of an aortic, or mitral heart valve.

In another aspect the disclosure relates to a method for visualizing the positioning of a prosthesis as disclosed herein wherein i. the prosthesis is delivered by appropriate means close or relatively close to the target implantation site; ii. the prosthesis is approached to its final target site; iii. the movement of the prosthesis is stopped when the deformable indicator means indicate contact with the tissue of the final target site; and the prosthesis is fully deployed at its final target site.

In yet another aspect the disclosure relates to a method for implantation of a heart valve prosthesis to a target site of an individual using a suitable catheter means and a heart valve prosthesis as described herein.

The prostheses as described herein may exhibit one or a number of advantages.

Known implants result in a pacemaker need of about 15 to 30%. In some embodiments of the present disclosure, the prosthesis is designed to reduce the need for pacemaker implantation after aortic heart valve replacement therapy by increasing the distance from the stent scaffold to the bundle of His. The corresponding need for pacemaker implantation may be less than 15%, such as less than 10% or even less than 8%.

Moreover, in embodiments wherein the design may exhibit a non-symmetric geometry in terms of the stent and the sealing material, the prosthesis may show little or no leakage, which may be unexpected for a non-symmetric design. One advantageous feature may be that in the area of the NC either the proximal section is shortened vis-à-vis the RC and LC section or the proximal part of the NC may be characterized by an indentation in direction towards the inner area of the prosthesis.

Various advantages of prosthesis as disclosed may be at least partly achieved by the design, features, and/or placement of locators, which may provide for a secure and/or precise positioning at the target site, e.g., in an advantageous manner such that they make sure that endogenous functions of the heart are satisfactory, like coronary artery function, bundle of His function, the valve as such with regard to functionality of the replacement valve, and the issue of leakage are met.

In particular the design and functionality of the locators, which may be, e.g., one, two, three or more locators, in the prosthesis and the foreshortening and the designed dimensions of the three sections of the prosthesis in relation to each other, the dimensions of the foreshortening as such and the dimensions of the proximal part of the prosthesis as well as the symmetry may contribute to various advantageous functional characteristics of the prosthesis as disclosed herein.

The attachment or design of the locators in an exemplary embodiment may be chosen to be in the middle area of the stent component. In addition the design of the locator, e.g., as an arch, may provide for a foreshortening that may be advantageous in view of a precise and proper positioning of the prosthesis.

The indicator means may be positioned or connected with the medical device in a manner so that it may make contact with the appropriate body compartment(s) or body part(s) during the implantation procedure so as to indicate correct and precise positioning of the medical device. It may comprise or consist of one or more wires or antennas.

In one embodiment the disclosure includes an indicator means and a so called counterpart means wherein these two parts are designed to be capable to contact each other.

In some embodiments, the prosthesis as described herein inter alia may be useful and may facilitate the correct positioning of a prosthesis at the target site and may avoid misplacement, e.g., based solely upon tactile feedback.

In one embodiment the prosthesis as disclosed comprises i. a shortened proximal section 17 or ii. it exhibits an indentation or open area in the proximal area of section 17, iii. the distal sections 16, 18 have either an open area at the areas where they are contacting the coronary arteries or the stent in this area does not contain a covering, or the distal section has a length in these sections that does not extend in its final positioning at the target site towards the coronary arteries, iv. a non-symmetrical sealing means in design version i.), v. three locator means designed as arches connected at their ends with fastening arches, and vi. a foreshortening of 5 mm.

Such an embodiment may be advantageous in terms of less interference with the endogenous heart function, may provide sufficient and/or good sealing features, and may be correctly positioned by way of minimally invasive catheter delivery.

LIST OF REFERENCE NUMBERS

1 Bundle of His
2 Septum
3 Mitral Valve
4 leaflet (RC) of aortic valve
5 leaflet (LC) of aortic valve
6 leaflet (NC) of aortic valve
7 annulus
8 aortic arch
9 RC (right coronary) sinus
10 NC (nucleus coronary) sinus
11 LC (left coronary) sinus
12 left coronary artery
13 right coronary artery
14 aortic heart valve prosthesis
15 sealing means
16 first section of prosthesis
17 second section of prosthesis
18 third section of prosthesis
19 area without stent and sealing means or designed as indentation
20 locator means
21 proximal section (preferred as stent ring)
21' proximal end
22 distal stent section
23 fastening arch
24 foreshortening distance/length
25 indicator means
26 positioning direction of prosthesis
27 aortic cusp
28 locator cover
29 radio-opaque marker
30 sinus of vasalva
31 calcified aortic leaflets
32 left ventricle
D distance of proximal end of locator means and proximal end of prosthesis

The invention claimed is:

1. A heart valve prosthesis, comprising:
a stent component comprising a scaffold including cells proximate a proximal end of the stent component,
a valve component coupled to an inner surface of the stent component,
a seal coupled to an outer surface of the stent component,
at least one locator pointing in a proximal direction for positioning the prosthesis at a target site of an endogenous heart valve, and
an indicator extending in the proximal direction and configured to move relative to the locator upon contact with the target site,
wherein the prosthesis is expandable from a non-expanded state to an expanded state, a shortest distance from a proximal end of the locator to a proximal end of the prosthesis being less in the expanded state than a shortest distance from the proximal end of the locator to the proximal end of the prosthesis in the non-expanded state,
wherein, in the non-expanded state, the proximal end of the locator radially overlaps at least a portion of the cells, and
wherein, in the expanded state, the shortest distance between the proximal end of the locator and the proximal end of the prosthesis is greater than zero and less than 10 mm.

2. The prosthesis according to claim 1, wherein the locator comprises a probe.

3. The prosthesis according to claim 1, wherein the distance between the proximal end of the locator and the proximal end of the prosthesis varies in a circumferential direction of the prosthesis.

4. The prosthesis according to claim 1, wherein in the non-expanded state, the locator and the stent component extend along a tube perimeter, and in the expanded state, the locator extends at least partially outside an expanded tube perimeter.

5. The prosthesis according to claim 1, wherein the locator comprises an arch attached to, or forming an integral part of, the stent component, and wherein the shortest distance between the proximal end of the locator and the proximal end of the stent component in the expanded state as compared to the non-expanded state differs by 1 mm, 2 mm, 3 mm, 4 mm, or 5 mm.

6. The prosthesis according to claim 5, wherein the arch of the locator has two ends, and wherein each end is attached to, or forms an integral part of, a fastening arch of the stent component.

7. The prosthesis according to claim 1, wherein the prosthesis is configured to not cover one or more coronary arteries when placed at the target site when in the expanded state.

8. The prosthesis according to claim 1, wherein the stent component comprises three sections including a first section that corresponds to a right coronary sinus (RCS), a second section that corresponds to a left coronary sinus (LCS), and a third section that corresponds to a non-coronary coronary sinus (NCS), wherein the three sections each comprise a distal end and a proximal end; and wherein:
the proximal end of each section extends with an equal length so that the sections corresponding to the RCS, LCS, and NCS end at the same level, or
the proximal ends corresponding to the RCS and LCS sections are shorter than the proximal end of the NCS section.

9. The prosthesis according to claim 8, wherein the proximal end of each section extends with an equal length so that the sections corresponding to the RCS, LCS, and NCS end at the same level, and wherein the NCS proximal section comprises an indentation.

10. The prosthesis according to claim 1, wherein the indicator comprises one or more wires or antennas.

11. The prosthesis according to claim 1, wherein the indicator comprises a radiopaque material.

12. The prosthesis according to claim 1, wherein the stent component comprises a counterpart to the indicator.

13. The prosthesis according to claim 12, wherein the counterpart comprises the at least one locator, a feeler, a hook, or a rim; and wherein the counterpart has a U, V, Y, M or W shape.

14. The prosthesis according to claim 13, wherein the indicator and the counterpart comprise the same materials.

15. The prosthesis according to claim 12, wherein the counterpart comprises a radiopaque material.

16. The prosthesis according to claim 1, wherein the stent component comprises nitinol, and the seal comprises soft fabric, textile, mammalian tissue, or a polymer.

17. The prosthesis according to claim 1, wherein the prosthesis is an aortic heart valve including three leaflets, or a mitral heart valve including two leaflets.

18. A heart valve prosthesis, comprising:
a stent component comprising a scaffold including cells proximate a proximal end of the stent component,
a valve component,
a seal configured to prevent reflux of blood between the prosthesis and an endogenous heart valve when the valve component is in a closed position,
at least one locator pointing in a proximal direction for positioning the prosthesis at a target site of the endogenous heart valve, the locator comprising an arch attached to, or forming an integral part of, the stent component, and
an indicator extending in the proximal direction and configured to move relative to the locator upon contact with the target site,
wherein the prosthesis is expandable from a non-expanded state to an expanded state, a shortest distance from a proximal end of the locator to a proximal end of the prosthesis being less in the expanded state than a shortest distance from the proximal end of the locator to the proximal end of the prosthesis in the non-expanded state,
wherein, in the non-expanded state, the proximal end of the locator radially overlaps at least a portion of the cells, and
wherein, in the expanded state, the proximal end of the locator does not radially overlap the cells and the shortest distance between the proximal end of the locator and the proximal end of the prosthesis is 1 mm to 5 mm.

* * * * *